(12) United States Patent
Haratake et al.

(10) Patent No.: US 11,138,735 B2
(45) Date of Patent: Oct. 5, 2021

(54) IMAGE PROCESSING APPARATUS AND MEDICAL IMAGE TAKING APPARATUS

(71) Applicant: CANON MEDICAL SYSTEMS CORPORATION, Otawara (JP)

(72) Inventors: Misaki Haratake, Utsunomiya (JP); Toshimitsu Kaneko, Kawasaki (JP); Atsushi Yaguchi, Taito (JP); Tatsuya Kimoto, Utsunomiya (JP); Shinsuke Tsukagoshi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 101 days.

(21) Appl. No.: 16/162,986

(22) Filed: Oct. 17, 2018

(65) Prior Publication Data
US 2019/0114772 A1 Apr. 18, 2019

(30) Foreign Application Priority Data

Oct. 17, 2017 (JP) .............................. JP2017-201218
Oct. 17, 2018 (JP) .............................. JP2018-195917

(51) Int. Cl.
*G06T 7/00* (2017.01)
*A61B 6/00* (2006.01)
(Continued)

(52) U.S. Cl.
CPC .......... *G06T 7/0016* (2013.01); *A61B 6/032* (2013.01); *A61B 6/463* (2013.01); *A61B 6/465* (2013.01);
(Continued)

(58) Field of Classification Search
USPC ................................................ 382/106–228
See application file for complete search history.

(56) References Cited

U.S. PATENT DOCUMENTS 5,768,413 A * 6/1998 Levin ....................... G06T 7/12
 382/131
6,473,698 B1 * 10/2002 Albert .................. A61B 5/0261
 702/19
(Continued)

FOREIGN PATENT DOCUMENTS

JP 2012-213604 11/2012
JP 2014-064913 4/2014
(Continued)

*Primary Examiner* — Marcellus J Augustin
(74) *Attorney, Agent, or Firm* — Oblon, McClelland, Maier & Neustadt, L.L.P.

(57) ABSTRACT

An image processing apparatus includes processing circuitry configured: to obtain a plurality of images taken so as to include a target site of a subject in temporal phases; and to calculate an index indicating a state of an adhesion at a boundary between a first site of the subject corresponding to a first region and a second site of the subject corresponding to a second region, by using classification information used for classifying each of pixels into one selected from between a first class related to the first region and a second class related to a second region positioned adjacent to the first region in a predetermined direction, on a basis of mobility information among the images in the temporal phases with respect to the pixels in the images that are arranged in the predetermined direction across the boundary between the first region and the second region of the images.

13 Claims, 13 Drawing Sheets

(51) Int. Cl.
  *A61B 6/03* (2006.01)
  *G06T 11/00* (2006.01)
  *G06T 7/11* (2017.01)
  *G06T 7/246* (2017.01)
  *G06K 9/00* (2006.01)

(52) U.S. Cl.
  CPC .......... *A61B 6/5217* (2013.01); *A61B 6/5288* (2013.01); *G06K 9/00* (2013.01); *G06T 7/11* (2017.01); *G06T 7/246* (2017.01); *G06T 11/005* (2013.01); *A61B 6/037* (2013.01); *A61B 6/461* (2013.01); *A61B 6/503* (2013.01); *A61B 6/541* (2013.01); *G06T 2207/10081* (2013.01); *G06T 2207/20072* (2013.01); *G06T 2207/30061* (2013.01); *G06T 2211/412* (2013.01)

(56) References Cited

U.S. PATENT DOCUMENTS

| | | | |
|---|---|---|---|
| 7,903,860 B2 * | 3/2011 | Grasruck | G06T 5/50 382/132 |
| 8,290,223 B2 * | 10/2012 | Suliga | G06K 9/4671 382/128 |
| 9,738,937 B1 * | 8/2017 | Hsieh | C12Q 1/6886 |
| 2012/0250966 A1 | 10/2012 | Fujisawa et al. | |
| 2013/0044808 A1 * | 2/2013 | Nakagawa | H04N 19/105 375/240.03 |
| 2014/0099014 A1 * | 4/2014 | Kii | G06T 7/62 382/133 |
| 2015/0173721 A1 | 6/2015 | Satoh et al. | |
| 2016/0027179 A1 * | 1/2016 | Takama | G06T 7/33 382/128 |
| 2016/0073994 A1 * | 3/2016 | Fujisawa | A61B 6/5217 382/131 |
| 2016/0180528 A1 | 6/2016 | Reynolds | |
| 2017/0061641 A1 * | 3/2017 | Inoue | G06T 7/246 |
| 2017/0309026 A1 | 10/2017 | Sakamoto et al. | |

FOREIGN PATENT DOCUMENTS

| | | |
|---|---|---|
| JP | 2016-067832 | 5/2016 |
| JP | 2016-116867 | 6/2016 |

* cited by examiner

IMAGE PROCESSING APPARATUS AND MEDICAL IMAGE TAKING APPARATUS

CROSS-REFERENCE TO RELATED APPLICATIONS

This application is based upon and claims the benefit of priority from Japanese Patent Application No. 2017-201218, filed on Oct. 17, 2017; and Japanese Patent Application No. 2018-195917, filed on Oct. 17, 2018 the entire contents of which are incorporated herein by reference.

FIELD

Embodiments described herein relate generally to an image processing apparatus and a medical image taking apparatus.

BACKGROUND

Conventionally, a medical image taking apparatus is known that is configured to evaluate the state of a conglutination of the parietal pleura and the visceral pleura of the lung, by using a moving image taken during respiration of an examined subject.

DETAILED DESCRIPTION

An image processing apparatus according to an embodiment includes processing circuitry. The processing circuitry is configured to obtain a plurality of images taken so as to include a target site a subject in a plurality of temporal phases. The processing circuitry is configured to calculate an index indicating a state of an adhesion at a boundary between a first site of the subject corresponding to a first region and a second site of the subject corresponding to a second region, by using classification information used for classifying each of a plurality of pixels into one selected from between a first class related to the first region and a second class related to a second region positioned adjacent to the first region in a predetermined direction, on a basis of mobility information among the images in the plurality of temporal phases with respect to the plurality of pixels in the images that are arranged in the predetermined direction across the boundary between the first region and the second region of the images.

Exemplary embodiments of an image processing apparatus and a medical image taking apparatus will be explained below, with reference to the accompanying drawings. Further, the description of each of the embodiments is, in principle, applicable to any other embodiment.

The term "medical image taking apparatus" is a generic term for any medical image diagnosis apparatus configured to generate a medical image by taking an image of an examined subject. For instance, examples of the medical image taking apparatus include X-ray CT apparatuses. In the embodiments described below, an example in which the present disclosure is applied to an X-ray CT apparatus will be explained; however, the present disclosure is similarly applicable to other medical image taking apparatuses (e.g., Magnetic Resonance Imaging [MRI] apparatuses, X-ray angiography apparatuses, Positron Emission Tomography [PET] apparatuses, Single Photon Emission Computed Tomography [SPECT] apparatuses).

First Embodiment

Figure 1:
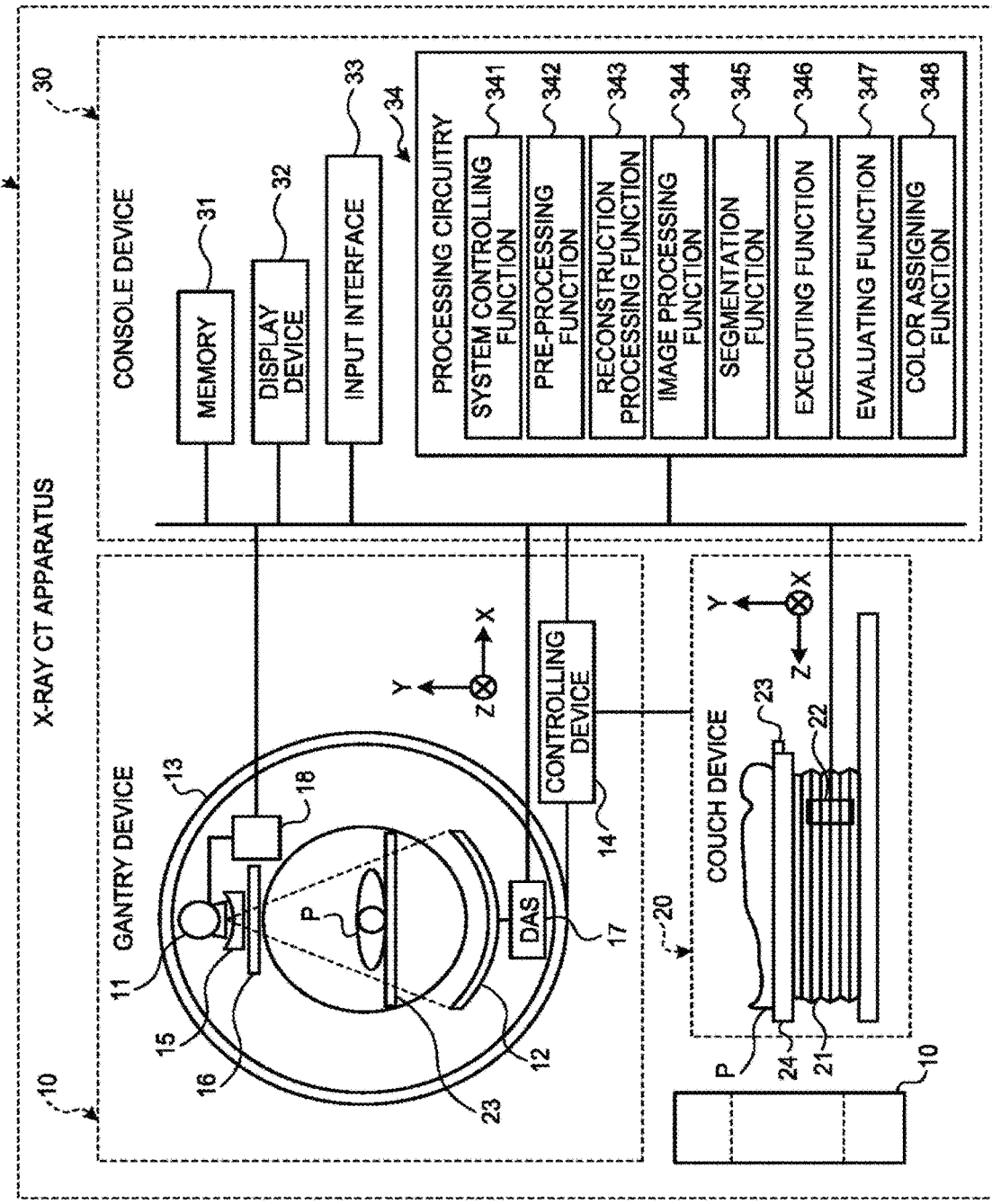
FIG. 1 is a diagram illustrating an exemplary configuration of an X-ray Computed Tomography (CT) apparatus according to a first embodiment.

FIG. 1 is a diagram illustrating an exemplary configuration of an X-ray CT apparatus 1 according to a first embodiment. As illustrated in FIG. 1, the X-ray CT apparatus 1 according to the first embodiment includes a gantry device 10, a couch device 20, and a console device 30. The gantry device 10, the couch device 20, and the console device 30 are connected together so as to be able to communicate with one another.

In the present embodiment, the longitudinal direction of the rotation axis of a rotating frame 13 in a non-tilted stat or of a couchtop 23 of the couch device 20 is defined as a "Z-axis direction". Further, the axial direction that is orthogonal to the Z-axis direction and is parallel to a floor surface is defined as an "X-axis direction". Further, an axial direction that is orthogonal to the Z-axis direction and is perpendicular to the floor surface is defined as a "Y-axis direction".

The gantry device 10 is a device configured to radiate X-rays onto an examined subject (hereinafter "subject") P, to detect X-rays that have passed through the subject P, and to output a detection result to the console device 30. The gantry device 10 includes an X-ray tube 11, an X-ray detector 12, the rotating frame 13, a controlling device 14, a wedge 15, a collimator 16, a Data Acquisition System (DAS) 17, and an X-ray high voltage device 18.

The X-ray tube 11 is a vacuum tube configured to emit thermo electrons from a negative pole (a filament) toward a positive pole (a target), by applying the high voltage supplied from the X-ray high voltage device 18. The X-ray tube 11 is configured to generate the X-rays by causing the thermo electrons to collide with the positive pole.

The wedge 15 is a filter used for adjusting the dose of the X-rays radiated from the X-ray tube 11. More specifically, the wedge 15 is a filter configured to pass and attenuate the X-rays radiated from the X-ray tube 11, so that the distribution of the X-rays radiated from the X-ray tube 11 onto the subject P is a predetermined distribution. For example, the wedge 15 may be a filter obtained by processing aluminum so as to have a predetermined target angle and a predetermined thickness. The wedge 15 may be referred to as a wedge filter or a bow-tie filter.

The collimator 16 is configured with lead plates or the like used for narrowing down the radiation range of the X-rays that have passed through the wedge 15. The collimator 16 is formed as slits by combining the plurality of lead plates or the like.

The X-ray detector 12 is configured to detect the X-rays that were radiated from the X-ray tube 11 and have passed through the subject P and to output an electrical signal corresponding to the detected X-ray dose to the DAS 17. For example, the X-ray detector 12 includes a plurality of rows of X-ray detecting elements in each of which a plurality of X-ray detecting elements are arranged in a channel direction along an arc centered on a focal point of the X-ray tube 11. For example, the X-ray detector 12 has a structure in which the plurality of rows of X-ray detecting elements are arranged in a slice direction (a row direction), the rows each being made up of the plurality of X-ray detecting elements arranged in the channel direction.

Further, for example, the X-ray detector 12 may be an indirect-conversion-type detector including a grid, a scintillator array, and an optical sensor array. The scintillator array includes a plurality of scintillators. Each of the scintillators includes a scintillator crystal configured to output light having photons in a quantity corresponding to the dose of the X-rays that have become incident thereto. The grid is arranged on such a surface of the scintillator array positioned the X-ray incident side and includes an X-ray blocking plate having a function of absorbing scattered X-rays. The optical sensor array has a function of outputting an electrical signal corresponding to the quantity of the light from the scintillators and includes, for example, an optical sensor such as a Photomultiplier Tube (PMT). Alternatively, the X-ray detector 12 may be a direct-conversion-type detector including a semiconductor element configured to convert X-rays that have become incident thereto into an electrical signal.

The X-ray high voltage device 16 includes a high voltage generating device having electric circuits such as a transformer and a rectifier and having a function of generating the high voltage to be applied to the X-ray tube 11 and an X-ray controlling device configured to control the output voltage corresponding to the output of the X-rays radiated by the X-ray tube 11. The high voltage generating device may use a transformer method or an inverter method. In this situation, the X-ray high voltage device 13 may be provided for the rotating frame 13 (explained later) or may be provided on the side of a fixed frame (not illustrated) of the gantry device 10. The fixed frame is a frame configured to rotatably support the rotating frame 13.

The DAS 17 includes an amplifier configured to perform an amplifying process on the electrical signals output from the X-ray detecting elements included in the X-ray detector 12 and an Analog/Digital (A/D) converter configured to convert the electrical signals into digital signals. The DAS 17 is configured to generate detection data. The detection data generated by the DAS 17 is transferred to the console device 30.

The rotating frame 13 is an annular frame configured to support the X-ray tube 11 and the X-ray detector 12 so as to oppose each other and configured to cause the controlling device 14 (explained later) to rotate the X-ray tube 11 and the X-ray detector 12. In addition to the X-ray tube 11 and the X-ray detector 12, the rotating frame 13 is further provided with, and is configured to support, the X-ray high voltage device 18 and the DAS 17. Further, the detection data generated by the DAS 17 is transmitted through optical communication from a transmitter including a Light Emitting Diode (LED) and being provided for the rotating frame 13, to a receiver including a photo diode and being provided in a non-rotating part (e.g., the fixed frame) of the gantry device 10, so as to be further transferred to the console device 30. The method for transmitting the detection data from the rotating frame 13 to the non-rotating part of the gantry device 10 is not limited to the optical communication mentioned above, and it is acceptable to use any contactless data transmission method.

The controlling device 14 includes processing circuitry having a Central Processing Unit (CPU) or the like and a driving mechanism configured with a motor and an actuator or the like. The controlling device 14 has a function of receiving an input signal from an input interface attached to either the console device 30 or the gantry device 10 and of controlling operations of the gantry device 10 and the couch device 20. For example, in response to the received input signal, the controlling device 14 exercises control to rotate the rotating frame 13, control to tilt the gantry device 10, and control to operate the couch device 20 and the couchtop 23. The control to tilt the gantry device 10 is realized by the controlling device 14 configured to rotate the rotating frame 13 centered on an axis extending parallel to the X-axis direction, according to tilt angle information input thereto by an input interface attached to the gantry device 10. In this situation, the controlling device 14 may be provided for the gantry device 10 or may be provided for the console device 30.

The couch device 27 is a device on which the subject P to be scanned is placed and which is configured to move the subject P. The couch device 20 includes a base 21, a couch driving device 22, a couchtop 23, and a supporting frame 24. The base 21 is a casing configured to support the supporting frame 24 so as to be movable in vertical directions. The couch driving device 22 is either a motor or an actuator configured to move the couchtop 23 on which the subject P is placed, in the long-axis directions of the couchtop 23. The couchtop 23 provided on the top face of the supporting frame 24 is a plate on which the subject P is placed. In addition to the couchtop 23, the couch driving device 22 may also be configured to move the supporting frame 24 in the long-axis directions of the couchtop 23.

The console device 30 is a device configured to receive operations performed by an operator on the X-ray CT apparatus 1 and to reconstruct CT image data by using the detection data acquired by the gantry device 10. As illustrated in FIG. 1, the console device 30 includes a memory 31, a display device 32, an input interface 33, and processing circuitry 34. The memory 31, the display device 32, the input interface 33, and the processing circuitry 34 are connected together so as to be able to communicate with one another.

The memory 31 is realized by using, for example, a semiconductor memory element such as a Random Access Memory (RAM), a flash memory, or the like, or a hard disk, an optical disk, or the like. For example, the memory 31 is configured to store therein projection data and the CT image data.

The display device 32 is configured to display various types of information. For example, the display device 32 is configured to output a medical image (a CT image) generated by the processing circuitry 34, a Graphical User Interface (GUI) used for receiving various types of operations from the operator, and the like. For example, the display device 32 may be a liquid crystal display device or a Cathode Ray Tube (CRT) display device.

The input interface 33 is configured to receive various types of input operations from the operator, to convert the received input operations into electrical signals, and to output the electrical signals to the processing circuitry 34. For example, the input interface 33 receives, from the operator, acquisition conditions used for acquiring the projection data, reconstruction conditions used for reconstructing the CT image data, image processing conditions used for generating a post-processing image from the CT image, and the like. For example, the input interface 33 is realized by using a mouse, a keyboard, a trackball, a switch, a button, a joystick, and/or the like.

The processing circuitry 34 is configured to control operations of the entirety of the X-ray CT apparatus 1. For example, the processing circuitry 34 is configured to execute a system controlling function 341, a pre-processing function 342, a reconstruction processing function 343, and an image processing function 344. Further, in the present embodiment, the processing circuitry 34 is also configured to execute a segmentation function 345, an executing function 346, an evaluating function 347, and a color assigning function 348. The processing circuitry 34 is realized by using a processor. The segmentation function 345 is an example of a segmentation processing unit. The executing function 346 is an example of an executing unit. The evaluating function 347 is an example of an evaluating unit.

In this situation, for example, the functions of the constituent elements of the processing circuitry 34, namely, the system controlling function 341, the pre-processing function 342, the reconstruction processing function 343, the image processing function 344, the segmentation function 345, the executing function 346, the evaluating function 347, and the color assigning function 348, are stored in the memory 31 in the form of computer-executable programs. The processing circuitry 34 is configured to realize the functions by reading the programs from the memory 31 and executing the read programs. In other words, the processing circuitry 34 that has read the programs has the functions illustrated within the processing circuitry 34 in FIG. 1.

Further, the example is explained above in which the single piece of processing circuitry (the processing circuitry 34) realizes the functions mentioned above; however, another arrangement is also acceptable in which the processing circuitry 34 is structured by combining together a plurality of independent processors, so that the functions are realized as a result of the processors executing the programs.

The term "processor" denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 31. In this situation, instead of saving the programs in the memory 31, it is also acceptable to directly incorporate the programs in the circuits of the processors. In that situation, the processors realize the functions by reading and executing the programs incorporated in the circuits thereof. Further, the processors do not each necessarily have to be structured as a single circuit. It is also acceptable to structure one processor by combining together a plurality of independent circuits so as to realize the functions thereof. Further, it is also acceptable to integrate two or more of the constituent elements into one processor so as to realize the functions thereof.

The system controlling function 341 is configured to control the various types of functions of the processing circuitry 34, on the basis of an input operation received from the operator via the input interface 33. For example, the system controlling function 341 is configured to control a CT scan performed by the X-ray CT apparatus 1. Further, by controlling the pre-processing function 342, the reconstruction processing function 343, and the image processing function 344, the system controlling function 341 is configured to control CT image data generating and displaying processes performed by the console device 30. The system controlling function 341 configured to exercise such display control is an example of a display controlling unit.

The pre-processing function 342 is configured to generate data obtained by performing, on the detection data output from the DAS 17, one or more pre-processing processes such as a logarithmic conversion process, an offset correcting process, an inter-channel sensitivity correcting process, a beam hardening correcting process, and/or the like. The data (the detection data) before the pre-processing processes and the data after the pre-processing processes may collectively be referred to as projection data.

The reconstruction processing function 343 is configured to generate the CT image data (reconstructed image data) by implementing a reconstructing process that uses a filter correction back projection method or a successive approximation reconstruction method on the projection data generated by the pre-processing function 342.

On the basis of an input operation received from the operator via the input interface 33, the image processing function 344 is configured to convert the CT image data generated by the reconstruction processing function 343 into tomography image data on an arbitrary cross-sectional plane or three-dimensional image data, by using a publicly-known method. In this situation, the three-dimensional image data is structured with a plurality of pixels (voxels).

Further, in the present embodiment, the image processing function 344 is configured to convert pieces of CT image data corresponding to a plurality of temporal phases into pieces of three-dimensional image data corresponding to a plurality of temporal phases. These pieces of three-dimensional image data corresponding to the plurality of temporal phases are what is called four-dimensional image data and may be obtained by, for example, performing a CT scan multiple times in mutually-different temporal phases on mutually the same region including a target site of the subject P.

Alternatively, the four-dimensional image data may be generated by the reconstruction processing function 343 mentioned above. For example, the image processing function 344 or the reconstruction processing function 343 according to the present embodiment is configured to generate the four-dimensional image data taken so as to include the target site of the subject P in the plurality of temporal phases. In other words, the four-dimensional image data is data obtained by taking images of the target site of the subject P. The image processing function 344 and the reconstruction processing function 343 are each an example of a generating unit.

Details of the segmentation function 345, the executing function 346, the evaluating function 347, and the color assigning function 348 will be explained later.

Incidentally, during surgery to remove a tumor such as lung cancer, the lung field parenchyma may be removed in units of pulmonary lobes or pulmonary segments in some situations. In those situations, it is necessary to remove the lung field parenchyma after detaching the pleura from the lung field parenchyma. Usually, it is possible to easily detach the pleura from the lung field parenchyma by simply pressing a surgical instrument against the pleura. However, when the pleura is adhering to the lung field parenchyma, it is necessary to detach the pleura from the lung field parenchyma while burning the adhesion location. In this situation, for example, the term "adhesion" refers to a situation in which a tissue sticks to another tissue. Examples of the "adhesion" include a situation in which a tissue in one site sticks to a tissue in another site and a situation in which a tissue and another tissue in mutually the same site stick to each other. Further, examples of the "adhesion" include "conglutination" and "infiltration".

To cope with the circumstances described above, it may be possible to allow the practitioner to assess whether or not the pleura is adhering to the lung field, by causing an ultrasound diagnosis apparatus to display, on a display device and in a real-time manner, an ultrasound image rendering the lung field and the pleura of the subject, immediately before the removal surgery. However, in that situation, it would be difficult for the practitioner to assess whether or not an adhesion is occurring in such an area where ultrasound waves cannot reach, e.g., the hidden side of the ribs and the vicinity of the heart of the subject. Also, when an adhesion is occurring on the mediastinum side, the practitioner might need a help from the field of cardiac surgery. However, because ultrasound waves do not easily reach the mediastinum, it would be difficult to assess the extent of the adhesion. As a result, there would be a delay in requesting a help from a medical doctor in the field of cardiac surgery.

These problems may similarly occur not only when the pleura is adhering to the lung field, but also when an adhesion is occurring in any other target site. For example, these problems may similarly occur when the parietal pleura is adhering to the visceral pleura, the parietal pleura and the visceral pleura structuring the pleura.

To cope with these problems, for example, it is possible to configure an image processing apparatus in the manner described below so as to make it possible to assess the state of a conglutination even in an area where ultrasound waves cannot reach. For example, it is possible to configure an image processing apparatus so as to set a reference point in each of two target sites, to calculate the magnitude of the difference between mobile vectors at the two reference points, and when the magnitude of the difference is equal to or smaller than a threshold value, to assess that two target sites are conglutinating with each other. In the following sections, a medical image processing apparatus configured in this manner will be explained as an image processing apparatus according to a comparison example.

In this regard, however, respiratory volumes significantly vary among subjects. For this reason, when the respiratory volume of the subject is relatively small, the magnitude of the difference between the mobile vectors at the two reference points may be equal to or smaller than the threshold value in some situations, even if no conglutination has occurred. In those situations, there is a possibility that the image processing apparatus according to the comparison example may erroneously assess that a conglutination has occurred.

As another example, when two target sites are conglutinating with each other in one point, the magnitude of the difference between the mobile vectors at the two reference points may be larger than the threshold value in some situations. For example, when two target sites are conglutinating with each other in one point, because one target site moves relative to the other target site in the manner of a pendulum, the one target site moves with hardly any impact of the moving of the other target site. In that situation, there is a possibility that the image processing apparatus according to the comparison example may erroneously assess that no conglutination has occurred, although the conglutination has occurred.

To cope with these situations, the X-ray CT apparatus 1 according to the first embodiment is configured to perform an evaluating process as explained below, for the purpose of evaluating, with an excellent level of precision, the state of an adhesion of one of more sites (target sites) subject to an ad ion assessment. In this situation, the state of an adhesion in a target sates denotes, for example, a situation in which a tissue and another tissue in the target site are sticking to each other. In the following sections, an example will be explained in which, as an example of the state of adhesion, the state of a conglutination is evaluated. However, by using the same method, it is also acceptable to evaluate the state of other types of adhesions, such as the state of an infiltration.

Figure 2:
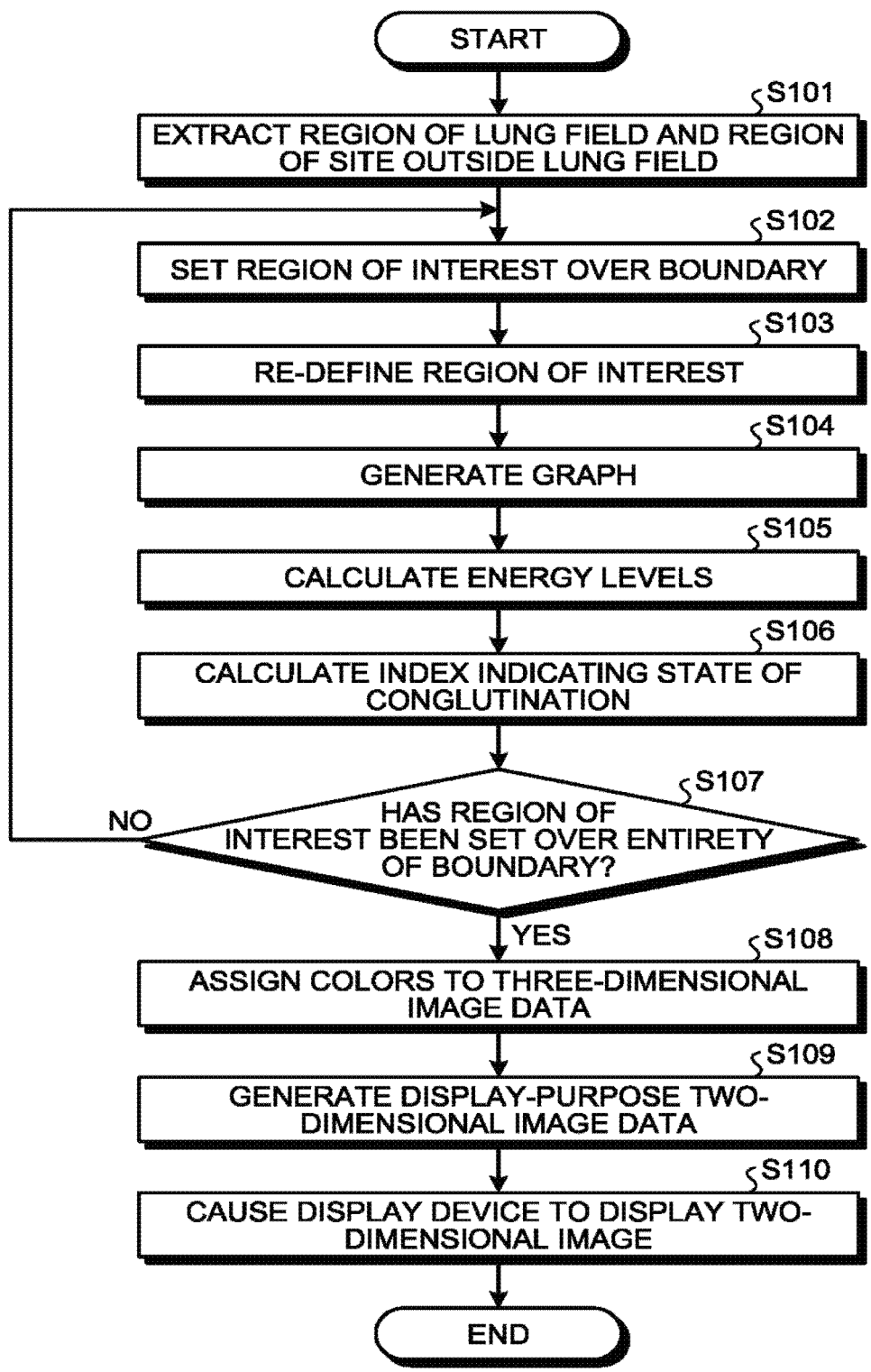
FIG. 2 is a flowchart illustrating a flow of an example of an evaluating process according to the first embodiment.

FIG. 2 is a flowchart illustrating a flow of an example of an evaluating process according to the first embodiment. For example, the evaluating process is performed by the system controlling function 341, the image processing function 344, the segmentation function 345, the executing function 346, the evaluating function 347, and the color assigning function 343, when the input interface 33 has received an instruction indicating that the evaluating process should be performed.

In FIG. 2, step S101 is a step corresponding to the segmentation function 345. Step S101 is a step at which the segmentation function 345 is realized as a result of the processing circuitry 34 invoking and executing the program corresponding to the segmentation function 345 from the memory 31. Steps S102 to S105 and S107 are steps corresponding to the executing function 346. Steps S102 to S105 and S107 are steps at which the executing function 346 is realized as a result of the processing circuitry 34 invoking and executing the program corresponding to the executing function 346 from the memory 31.

Step S106 is a step corresponding to the evaluating function 347. Step S106 is a step at which the evaluating function 347 is realized as a result of the processing circuitry 34 invoking and executing the program corresponding to the evaluating function 347 from the memory 31. Step S108 is a step corresponding to the color assigning function 348. Step S108 is a step at which the color assigning function 348 is realized as a result of the processing circuitry 34 invoking and executing the program corresponding to the color assigning function 348 from the memory 31.

Step S109 is a step corresponding to the image processing function 344. Step S109 is a step at which the image processing function 344 is realized as a result of the processing circuitry 34 invoking and executing the program corresponding to the image processing function 344 from the memory 31. Step S110 is a step corresponding to the system controlling function 341. Step S110 is a step at which the system controlling function 341 is realized as a result of the processing circuitry 34 invoking and executing the program corresponding to the system controlling function 341 from the memory 31.

In this situation, before the evaluating process is performed, pieces of three-dimensional image data in a plurality of temporal phases rendering a target site subject to a conglutination assessment are stored in the memory 31, in advance. Further, in the following sections, an example will be explained in which target sites are the lung field and a site outside the lung field. For example, the site outside the lung field includes the pleura. However, the target sites are not limited to those in the example. For instance, the target sites may be made on target sites represented by the parietal pleura and the visceral pleura. Further, as the pieces of three-dimensional image data in the plurality of temporal phases, the pieces of three-dimensional image data corresponding to T frames (where T is a natural number) are stored in the memory 31. In the present embodiment, a piece of three-dimensional image data in a K-th temporal phase (where K=1, . . . , T) corresponds to a piece of three-dimensional image data in a K-th frame.

As illustrated in FIG. 2, by performing a publicly-known segmentation process on a piece of three-dimensional image data in one temporal phase, the segmentation function 345 extracts a region of the lung field and a region of the site outside the lung field from the entire region of the piece of three-dimensional image data (step S101).

For example, at step S101, the segmentation function 345 obtains the pieces of three-dimensional image data in the plurality of temporal phases stored in the memory 31. Further, the segmentation function 345 selects a piece of three-dimensional image data in a predetermined temporal phase from among the pieces of three-dimensional image data in the plurality of temporal phases.

Figure 3:
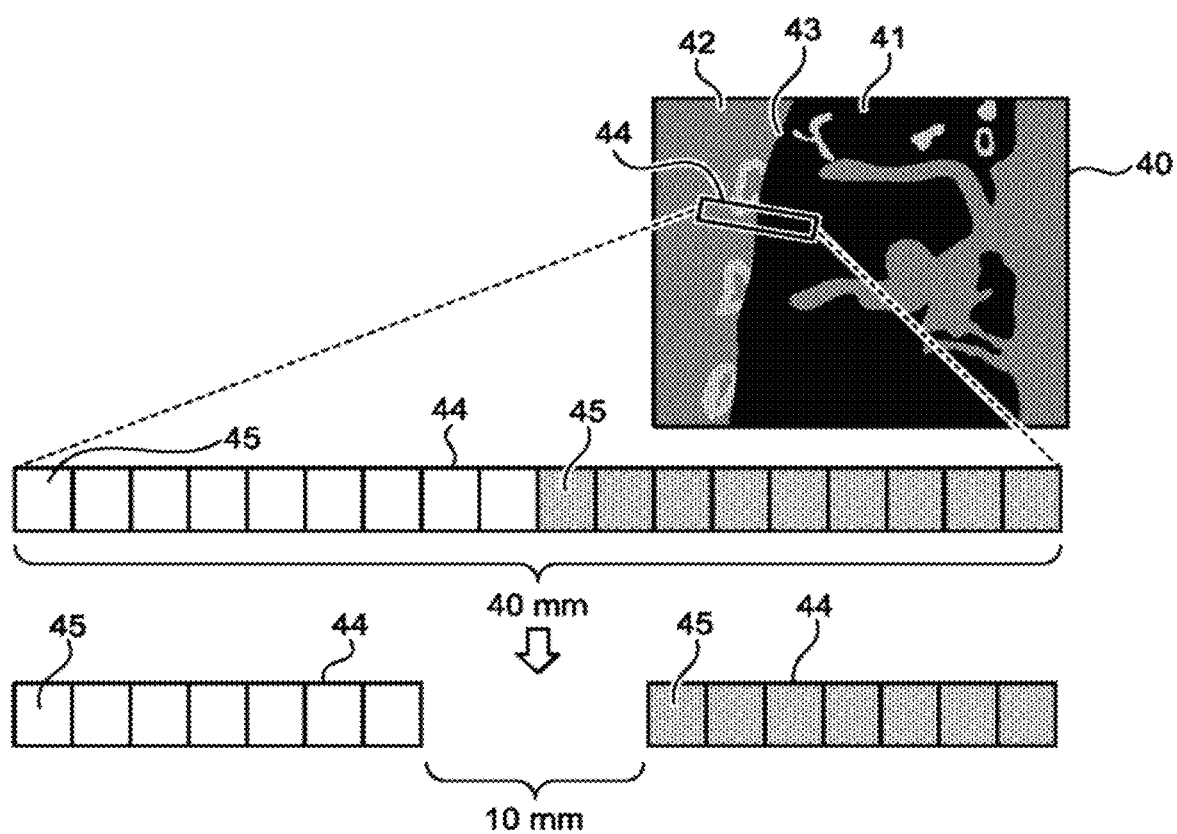
FIG. 3 is a drawing for explaining the example of the evaluating process according to the first embodiment.

FIG. 3 is a drawing for explaining an example of the evaluating process according to the first embodiment. For example, the segmentation function 345 selects a piece of three-dimensional image data 40 in the first temporal phase. An example will be explained herein in which the piece of three-dimensional image data 40 in the first temporal phase has been selected as the predetermined temporal phase. Subsequently, the segmentation function 345 extracts a region 41 of the lung field and a region 42 of the site outside the lung field, by performing the segmentation process on the selected piece of three-dimensional image data 40 in the first temporal phase. In other words, the segmentation function 345 performs the segmentation process to extract the region 41 of the lung field and the region 42 of the site outside the lung field from an image represented by the piece of three-dimensional image data 40. The region 42 of the site outside the lung field is an example of the first region. The region 41 of the lung field is an example of the second region. Further, the region 41 of the lung field is a region positioned adjacent to the region 42 of the site outside the lung field in the direction of the line normal to a boundary 43. Further, the site outside the lung field is an example of the first site. The lung field is an example of the second site.

Further, the executing function 346 sets a one-dimensional Region of Interest (ROI) 44 over the boundary 43 between the region 41 of the lung field and the region 42 of the site outside the lung field (step S102). To explain a specific example, the executing function 346 sets the region of interest 44 in such a manner that the longitudinal direction of the region of interest 44 extends along the direction of the line normal to the boundary 43, while the region of interest 44 contains a part of the boundary 43. In this manner, the region of interest 44 is set so that the longitudinal direction of the one-dimensional region of interest 44 and the boundary 43 are perpendicular to each other. Further, the region of interest 44 that was set in this manner contains a plurality of pixels 45 that are linearly (i.e., one-dimensionally) positioned. In other words, the plurality of pixels 45 of the image represented by the piece of three-dimensional image data 40 are arranged in the direction of the line normal to the boundary 43, across the boundary 43 between the region 41 of the lung field and the region 42 of the site outside the lung field. In this situation, the direction of the line normal to the boundary 43 is an example of the predetermined direction. In the present embodiment, the executing function 346 is configured to set the region of interest 44 in such a manner that a central part of the region of interest 44 in terms of the longitudinal direction is positioned at the boundary 43. However, the executing function 346 may be configured to set the region of interest 44 in such a manner that the central part of the region of interest 44 in terms of the longitudinal direction is not positioned at the boundary 43.

As illustrated in FIG. 3, for example, when the length of the region of interest 44 in the longitudinal direction is 40 mm, the plurality of pixels 45 arranged over the length of 40 mm are contained in the region of interest 44. In the following sections, an example will be explained in which the length of the region of interest 44 is 40 mm; however, the length of the region of interest 44 is not limited to 40 mm and may have any other value.

Subsequently, the executing function 346 re-defines the region of interest 44, by removing a predetermined region centered on the boundary 43, from the entire region of the region of interest 44 (step S103). For example, at step S103, as illustrated in FIG. 3, the executing function 346 removes a 10-mm region extending in the longitudinal direction of the region of interest 44 and being centered on the boundary 43, from the entire region of the region of interest 44 defined at step S102. The executing function 346 then defines the remaining region after the removal as a new region of interest 44.

As illustrated in FIG. 3, the re-defined region of interest 44 contains fourteen pixels 45. In the following sections, an example will be explained in which the number of pixels 45 contained in the region of interest 44 is fourteen; however, the number of pixels 45 contained in the region of interest 44 is not limited to that in this example. The pixels 45 contained in the re-defined region of interest 44 will be used in the various types of processes at step S104 and thereafter.

Alternatively, the executing function 346 may omit the process of re-defining the region of interest 44 at step S103. In that situation, the plurality of pixels 45 in the region of interest 44 set at step S102 will be used in the various types of processes at step S104 and thereafter.

Further, the executing function 346 performs the processes at steps S104 and S105 by performing a part of a clustering process for classifying the plurality of pixels 45 into a plurality of clusters. The clusters may be referred to as classes. In the present embodiment, the executing function 346 performs a part of a graph cut process (a graph cutting process, a graph cut method), which is an example of the clustering process.

Figure 4:
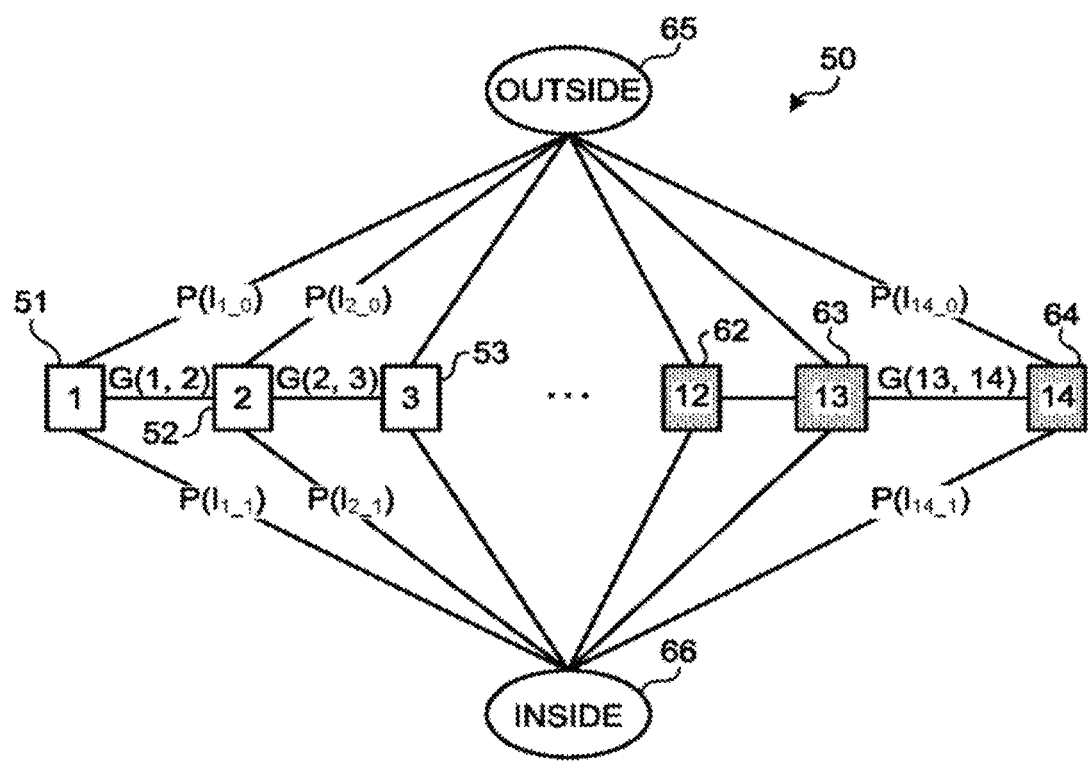
FIG. 4 is another drawing for explaining the example of the evaluating process according to the first embodiment.

FIG. 4 is another drawing for explaining the example of the evaluating process according to the first embodiment. To explain a specific example, as illustrated in FIG. 4, the executing function 346 generates a graph 50 including nodes 51 to 66 (step S104). The graph 50 is a graph in which, for example, each of the fourteen pixels 45 illustrated in FIG. 3 serves as a different one of the fourteen nodes 51 to 64. In FIG. 4, among the fourteen nodes 51 to 64, the eight nodes 54 to 61 are omitted from the drawing.

For example, the node 51 corresponds to the first pixel 45 from the left in FIG. 3. The other nodes 52 to 64 also respectively correspond to the other pixels in the same manner. In other words, among the fourteen nodes 51 to 64 arranged in a row from the left to the right in FIG. 4, a j-th node from the left (where j=1, 2, . . . , 14) corresponds to a j-th pixel 45 from the left in FIG. 3. In the following sections, the j-th pixel 45 from the left in FIG. 3 may be referred to as a "j-th pixel". Among the plurality of nodes 51 to 64 in FIG. 4, a j-th node from the left may be referred to as a "j-th node".

A node 65 corresponds to the region 42 of the site outside the lung field positioned on the outside of the boundary 43. A node 66 corresponds to the region 41 of the lung field positioned on the inside of the boundary 43.

Further, each of the plurality of nodes 51 to 64 is connected to the node 65 by a line (a line segment). Similarly, each of the plurality of nodes 51 to 64 is also connected to the node 66 by a line. Further, any two nodes that are positioned adjacent to each other are connected together by a line. In this situation, two nodes that are positioned adjacent to each other denote, for example, an n-th node (where n=1, 2, . . . , 13) and an (n+1)-th node.

At step S104, the executing function 346 sets a weight with each of the lines. At first, a weight $P(l_{j\_0})$ set with each of the lines connecting the plurality of nodes 51 to 64 to the node 65 will be explained. The weight $P(l_{j\_0})$ is set with the line connecting the j-th node to the node 65. In this situation, the weight $P(l_{j\_0})$ is an example of a value related to a cost that is used for classifying each of the plurality of pixels 45 into a first cluster (explained later) or a second cluster (explained later). For example, the weight $P(l_{j\_0})$ may be expressed by using Expression (1) presented below.

$$P(l_{j\_0})=-\log(p(l_j)) \quad (1)$$

In Expression (1), for example, $p(l_j)$ is a value from "0" to "1" inclusive. A specific example of $p(l_j)$ will be explained. As noted above, the node 65 corresponds to the region 42 of the site outside the lung field. For this reason, the executing function 346 performs a specific process so that a relatively large value is set to the weight $P(l_{j\_0})$ for each of the lines connecting the nodes 51 to 57 to the node 65, the nodes 51 to 57 corresponding to the seven pixels 45 positioned in the region 42 of the site outside the lung field illustrated in FIG. 3. The specific process is that the executing function 346 assigns "0.001" to $p(l_j)$ in Expression (1).

In contrast, the executing function 346 performs a specific process so that a relatively small value is set to the weight $P(l_{j\_0})$ for each of the lines connecting the nodes 58 to 64 to the node 65, the nodes 58 to 64 corresponding to the seven pixels 45 that are not positioned in the region 42 of the site outside the lung field illustrated in FIG. 3. The specific process is that the executing function 346 assigns "0.999" to $p(l_j)$ in Expression (1).

Next, a weight $P(l_{j\_1})$ set with each of the lines connecting the plurality of nodes 51 to 64 to the node 66 will be explained. The weight $P(l_{j\_1})$ is set with the line connecting the j-th node to the node 66. In this situation, the weight $P(l_{j\_1})$ is an example of a value related to a cost that is used for classifying each of the plurality of pixels 45 into the first cluster (explained later) or the second cluster (explained later). For example, the weight $P(l_{j\_1})$ may be expressed by using Expression (2) presented below.

$$P(l_{j\_1})=-\log(1-p(l_j)) \quad (2)$$

Next, a specific example of $p(l_j)$ in Expression (2) will be explained. As noted above, the node 66 corresponds to the region 41 of the lung field. For this reason, the executing function 346 performs a specific process so that a relatively large value is set to the weight $P(l_{j\_1})$ for each of the lines connecting the nodes 58 to 64 to the node 66, the nodes 56 to 64 corresponding to the seven pixels 45 positioned in the region 41 of the lung field illustrated in FIG. 3. The specific process is that the executing function 346 assigns "0.999" to $p(l_j)$ in Expression (2).

In contrast, the executing function 346 performs a specific process so that a relatively small value is set to the weight $P(l_{j\_1})$ for each of the lines connecting the nodes 51 to 57 to the node 66, the nodes 51 to 57 corresponding to the seven pixels 45 that are not positioned in the region 41 of the lung field illustrated in FIG. 3. The specific process is that the executing function 346 assigns "0.001" to $p(l_j)$ in Expression (2).

As a result, when calculating the weight $P(l_{j\_0})$ and the weight $P(l_{j\_1})$ with respect to the j-th node, the executing function 346 assigns mutually the same value to $p(l_j)$ in Expressions (1) and (2).

Next, a weight $G(n,n+1)$ set with a line connecting together two nodes adjacently positioned to each other will be explained. The weight $G(n,n+1)$ is set with a line connecting an n-th node and an (n+1)-th node to each other. For example, the weight $G(n,n+1)$ may be expressed by using Expression (3) presented below.

$$G(n, n+1) = \frac{1}{2} \cdot \frac{g(n, n+1)}{\frac{1}{N-1}\sum_{r=1}^{N-1} g(r, r+1)} \quad (3)$$

In Expression (3), "N" denotes the number of pixels 45 contained in the re-defined region of interest 44. As a specific example, the value of "N" is "14" in the present embodiment.

Further, $g(n,n+1)$ in Expression (3) may be expressed by using Expression (4) presented below.

$$g(n, n+1) = \frac{1}{T-1}\sum_{i=1}^{T-1} \|X_{n\_i} - X_{(n+1)\_i}\|_2 \quad (4)$$

In Expression (4), $X_{n\_i}$ denotes a motion vector (a mobile vector) of an n-th pixel. More specifically, $X_{n\_i}$ denotes a vector from the position of the n-th pixel in the three-dimensional image data in an i-th frame to the position of the n-th pixel in the three-dimensional image data in an (i+1)-th frame, where i=1, 2, . . . , T−1.

The same applies to $X_{(n+1)\_i}$. More specifically, $X_{(n+1)\_i}$ denotes a motion vector of an (n+1)-th pixel from the left in FIG. 3. For example, $X_{(n+1)\_i}$ denotes a vector from the position of the (n+1)-th pixel in the three-dimensional image data in the i-th frame to the position of the (n+1)-th pixel in the three-dimensional image data in the (i+1)-th frame.

In the present embodiment, the executing function 346 is able to calculate the motion vector $X_{n\_i}$ and the motion vector $X_{(n+1)\_i}$ mentioned above, by tracking the position of each of the plurality of pixels 45 from the three-dimensional image data of the first frame, up to the three-dimensional image data of the T-th frame. In this manner, the executing function 346 calculates the motion vector $X_{n\_i}$ and the motion vector $X_{(n+1)\_i}$ among the images in the plurality of temporal phases with respect to the plurality of pixels 45. In this situation, the motion vector $X_{n\_i}$ and the motion vector $X_{(n+1)\_i}$ are each an example of the mobility information.

Figure 5:
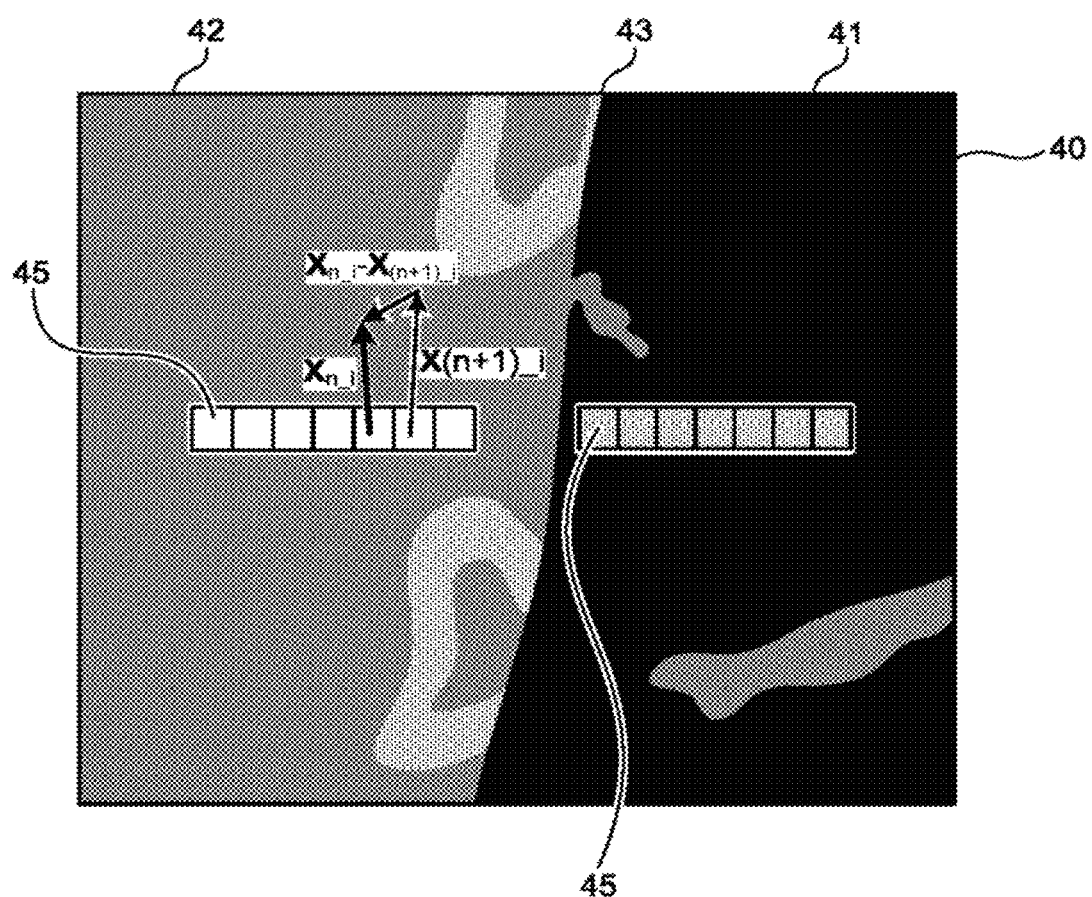
FIG. 5 is yet another drawing for explaining the example of the evaluating process according to the first embodiment.

FIG. 5 is yet another drawing for explaining the example of the evaluating process according to the first embodiment. As illustrated in FIG. 5 and Expression (4), the executing function 346 calculates the magnitude of a difference vector $(X_{n\_i}-X_{(n+1)\_i})$ between the motion vector $X_{n\_i}$ and the motion vector $X_{(n+1)\_i}$, between all the pairs made up of pieces of three-dimensional image data positioned adjacent to each other on the time axis. After that, as illustrated in Expression (4), the executing function 346 calculates g(n, n+1) by dividing the total sum of the calculated magnitudes of the plurality of difference vectors $(X_{n\_i}-X_{(n+1)\_i})$ by the total number (T−1) of the pairs made up of the pieces of three-dimensional image data positioned adjacent to each other on the time axis.

When two pixels (the n-th pixel and the (n+1)-th pixel) 45 positioned adjacent to each other move in the same manner as each other, the value g(n,n+1) is relatively small. In that situation, of the two pixels 45 positioned adjacent to each other, one of the pixels 45 is considered to be a pixel positioned in the region 41 of the lung field, whereas the other pixel 45 is considered to be a pixel positioned in the region 42 of the site outside the lung field. Alternatively, the two pixels 45 positioned adjacent to each other are considered to be both pixels positioned in either the region 41 of the lung field or the region 42 of the site outside the lung field. When the value of g(n,n+1) is relatively small, while one of the pixels 45 is positioned in the region 41 of the lung field, and the other pixel 45 is positioned in the region 42 of the site outside the lung field, it is considered that the lung field and the site outside the lung field of the subject P are conglutinating with each other.

In contrast, when the motions of the two pixels 45 positioned adjacent to each other are different from each other to a relatively large extent, the value of g(n,n+1) is relatively large. In that situation, of the two pixels 45 positioned adjacent to each other, one of the pixels 45 is considered to be a pixel positioned in the region 41 of the lung field, whereas the other pixel 45 is considered to be a pixel positioned in the region 42 of the site outside the lung field, and it is considered that the lung field and the site outside the lung field are not conglutinating with each other.

In Expression (3), the same explanation as with g(n,n+1) applies to g(r,r+1).

Incidentally, during a commonly-used graph cut process (a graph cut method), for the purpose of eventually classifying a plurality of pixels into a plurality of clusters, a graph is cut by each of a plurality of lines (hereinafter, "cut lines") so as to calculate an energy level for each of the cut lines. Further, during the commonly-used graph cut process, on the basis of the cut line having the smallest level of energy among the energy levels calculated in correspondence with the cut lines, a clustering process is performed to classify each of the pixels into one of a plurality of clusters.

In contrast, according to the present embodiment, although the executing function 346 performs the one part of the graph cut process, the executing function 346 does not perform the clustering process of eventually classifying each of the pixels 45 into a corresponding one of the plurality of clusters. By using Expression (5) presented below, the executing function 346 calculates energy levels $E(L_1, L_2, \ldots, L_N, w)$ in correspondence with the cut lines used for cutting the graph 50 (step S105).

$$E(L_1, L_2, \ldots, L_N, w) = E_d(L_1, L_2, \ldots, L_N) + \gamma E_s(w) \quad (5)$$

In Expression (5), "γ" denotes a coefficient having positive value.

Further, in Expression (5), when a cut line intersects the line connecting a c-th node to the node 65, Lc (c=1, 2, . . . , N) is set to "0". On the contrary, when a cut line intersects the line connecting a c-th node to the node 66, Lc is set to "1".

Further, in Expression (5), when a cut line intersects the line connecting a c-th node to a (c+1)-th node, "w" is set to "c". On the contrary, when a cut line does not intersect any of the lines connecting two nodes positioned adjacent to each other among the plurality of nodes 51 to 64, "w" is set to a predetermined value (e.g., a negative integer "−1") other than the positive integers from "1" to "N−1".

Further, in Expression (5), "$E_d(L_1, L_2, \ldots, L_N)$" may be expressed by using Expression (6) presented below.

$$E_d(L_1, L_2, \ldots, L_N) = \frac{1}{N}\sum_{j=1}^{N} P(l_{j\_}L_j) \quad (6)$$

The term "$E_d(L_1, L_2, \ldots, L_N)$" may be referred to as a data term and indicates an energy level based on the pixel values (the CT values) of the pixels 45. The higher the possibility of the boundary between the region of the lung field and the region of the site outside the lung field based on the cut line coinciding with the actual boundary between the region of the lung field and the region of the site outside the lung field of the subject P is, the smaller is the energy level.

Further, in Expression (5), "$E_s(w)$" may be expressed by using Expression (7) presented below.

$$E_s(w) = \exp(-G(w, w+1)) \quad (7)$$

The term "$E_s(w)$" may be referred to as a smoothing term and indicates an energy level taking the degree of smoothness of the boundary into consideration, while being independent of the data term described above. For example, using only the data term would make the energy level susceptible to noise because only the CT values are taken into consideration, and there would be a possibility that the boundary might not be smooth. However, using the smoothing term makes the boundary smooth. In this situation, in the term "$E_s(w)$", when "w" is set to the abovementioned predetermined value such as "−1", the value of "$E_s(-1)$" is 0.

Further, when the lung field and the site outside the lung field of the subject P are considered to be conglutinating with each other, the value of g(n,n+1) is relatively small, as mentioned above. Further, when the value of g(n,n+1) is smaller, the value of the smoothing term is larger. On the contrary, when the lung field and the site outside the lung field of the subject P are not considered to be conglutinating with each other, the value of g(n,n+1) is relatively large, and the value of the smoothing term is small.

Figure 6:
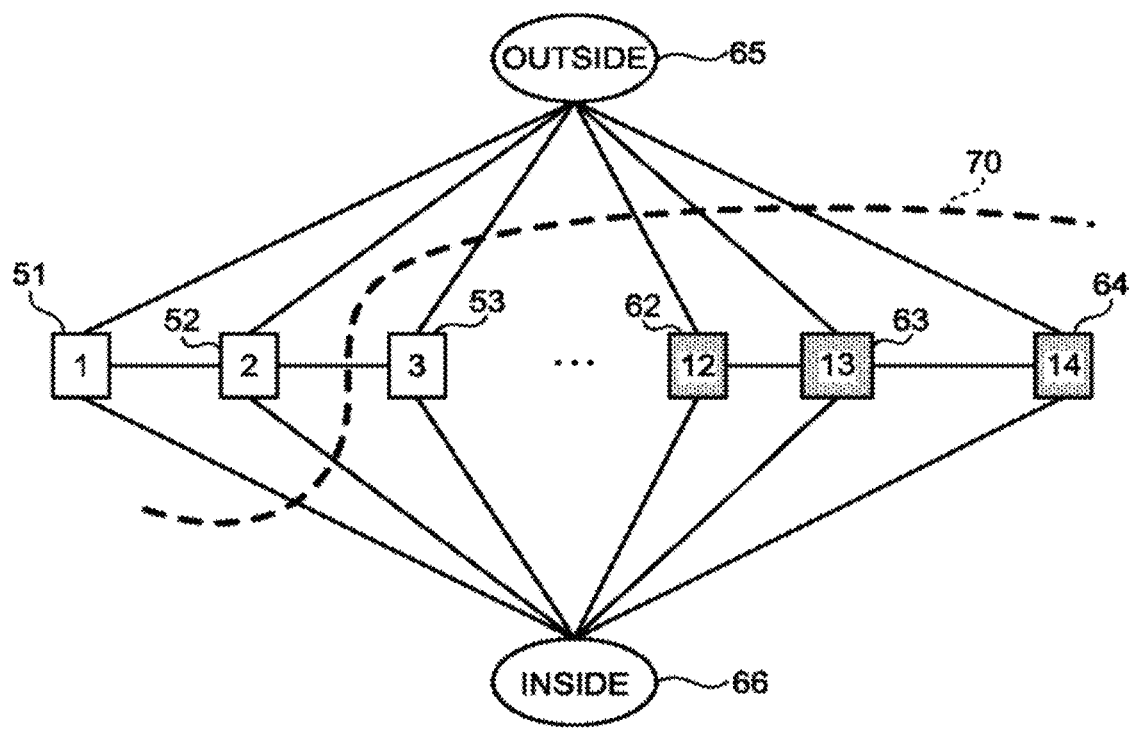
FIG. 6 is a drawing for explaining an example of a cut line according to the first embodiment.
Figure 7:
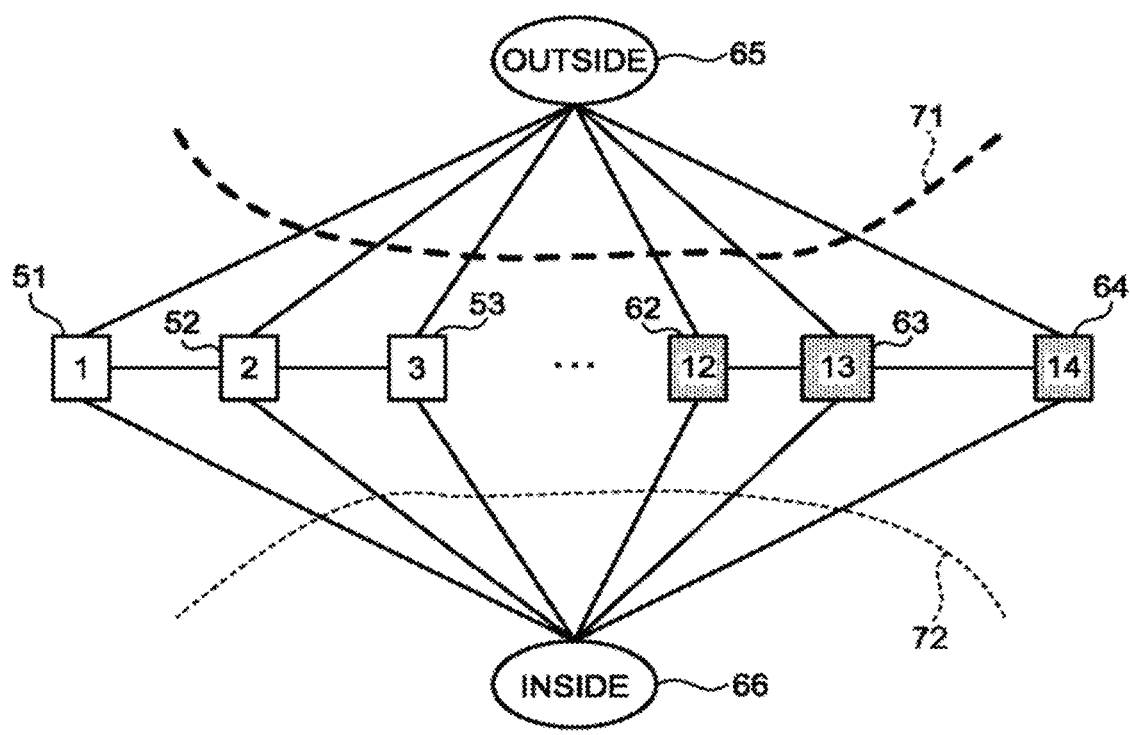
FIG. 7 is another drawing for explaining the example of the cut line according to the first embodiment.

FIGS. 6 and 7 are drawings for explaining an example of the cut line according to the first embodiment. As illustrated in FIG. 6, for example, the executing function 346 cuts the graph 50 with a cut line 70. The cut line 70 is a line used for classifying the fourteen pixels 45 in such a manner that the first and the second pixels belong to a cluster (the first cluster) corresponding to the region 42 of the site outside the lung field, while the third to the fourteenth pixels belong to a cluster (the second cluster) corresponding to the region 41 of the lung field. The first cluster may be referred to as a first class. The second cluster may be referred to as a second class.

Further, as illustrated in FIG. 7, the executing function 346 cuts the graph 50 with a cut line 71. The cut line 71 is a line used for classifying the fourteen pixels 45 in such a manner that the first to the fourteenth pixels belong to the second cluster. Further, the executing function 346 cuts the graph 50 with a cut line 72. The cut line 72 is a line used for classifying the fourteen pixels 45 in such a manner that the first to the fourteenth pixels belong to the first cluster. As illustrated in FIG. 7, the cut line 71 and the cut line 72 each do not intersect any of the lines connecting two nodes positioned adjacent to each other among the plurality of nodes 51 to 64.

In the present embodiment, the executing function 346 cuts the graph 50 with each of the fifteen cut lines in total, namely, thirteen cut lines each intersecting a line connecting a c-th node to a (c+1)-th node and the two cut lines 71 and 72 described above.

Further, for each of the cut lines, the executing function 346 calculates the energy level E ($L_1, L_2, \ldots, L_N$, w) by using Expression (5). As explained above, in the present embodiment, the executing function 346 calculates the energy levels E($L_1, L_2, \ldots, L_N$, w) in correspondence with the cut lines, but does not perform the clustering process of classifying each of the pixels 45 into a corresponding one of the clusters.

At steps S104 and S105, the executing function 346 performs the one part of the clustering process of classifying the plurality of pixels 45 into the plurality of clusters, on the basis of the motion vector of each of the plurality of pixels 45 in the region of interest 44 including the boundary 43 in the target site. For example, as the one part of the clustering process, the executing function 346 performs a process of calculating the motion vector of each of the plurality of pixels 45 and further calculating, with respect to each pair of two pixels 45 positioned adjacent to each other among the plurality of pixels 45, the magnitude of the difference vector ($X_{n\_i} - X_{(n+1)\_i}$) of the two motion vectors of the two pixels 45, on the basis of the calculated plurality of motion vectors. In this situation, the two pixels 45 positioned adjacent to each other are pixels that are positioned adjacent to each other in the direction of the line normal to the boundary 43.

Further, at steps S104 and S105, on the basis of the motion vector $X_{n\_i}$ and the motion vector $X_{(n+1)\_i}$, the executing function 346 calculates the energy levels E($L_1, L_2, \ldots, L_N$, w) used for classifying each of the plurality of pixels 45 into the first cluster related to the region 42 of the site outside the lung field or the second cluster related to the region 41 of the lung field. The energy levels E($L_1, L_2, \ldots, L_N$, w) are examples of the classification information. Further, the energy levels E($L_1, L_2, \ldots, L_N$, w) are also examples of the value related to a cost used for classifying each of the plurality of pixels 45 into one selected from between the first and the second cluster.

Further, the evaluating function 347 calculates an index indicating the state of a conglutination (step S106). A specific example will be explained. As the index indicating the state of the conglutination, the evaluating function 347 calculates a probability p, by using Expression (8) presented below, for example.

$$p = \frac{\exp(-E(0, \ldots, 0, -1)) + \exp(-E(1, \ldots, 1, -1))}{\sum \exp(-E(L_1, L_2, \ldots, L_N, w))} \quad (8)$$

In Expression (8), the denominator of the term on the right-hand side indicates the total sum of fifteen values of exp(-E($L_1, L_2, \ldots, L_N$, w)) with respect to the fifteen cut lines.

Further, in the numerator of the term on the right-hand side of Expression (8), exp(-E(0, \ldots, 0, -1)) denotes the energy level E($L_1, L_2, \ldots, L_N$, w) of the cut line 71 explained above, where $L_1 = L_2 = \ldots = L_N = 0$, whereas w=-1.

Further, in the numerator of the term on the right-hand side in Expression (8), exp(-E(1, \ldots, 1, -1)) denotes the energy level E($L_1, L_2, \ldots, L_N$, w) of the cut line 72 explained above, where $L_1 = L_2 = \ldots = L_N = 1$, whereas w=-1.

The probability p is a small value in the range from "0" to "1" inclusive. The probability p is, for example, a probability of the plurality of pixels 45 belonging to a single cluster (either the first cluster or the second cluster), when the clustering process is performed on the plurality of pixels 45 in the region of interest 44. Accordingly, the probability p is a value indicating the possibility of the site outside the lung field conglutinating with the lung field serving as the target site. The closer the value of the probability p is to "1", the higher is the possibility of the occurrence of the conglutination. It should be noted that the probability p does not indicate the degree of the conglutination.

As explained above, at step S106, the evaluating function 347 calculates, as indicated in Expression (8), the index indicating the state of the conglutination at the boundary 43 between the site outside the lung field of the subject P corresponding to the region 42 of the site outside the lung field and the lung field of the subject P corresponding to the region 41 of the lung field, on the basis of the energy levels E($L_1, L_2, \ldots, L_N$, w).

Further, at step S106, the evaluating function 347 calculates the index on the basis of the energy levels E($L_1, L_2, \ldots, L_N$, w) based on the magnitudes of the difference vectors ($X_{n\_i} - X_{(n+1)\_i}$) calculated at step S104. In other words, the evaluating function 347 calculates the index on the basis of the magnitudes of the calculated difference vectors ($X_{n\_i} - X_{(n+1)\_i}$).

FIGS. 8 to 13 are drawings for explaining an example of the evaluating process according to the first embodiment. FIGS. 8 to 13 illustrate the region of interest 44 that is set so as to include a part of the boundary 43 between the region 41 of the lung field and the region 42 of the site outside the lung field. FIGS. 6 to 13 illustrate an example in which the process of re-defining the region of interest 44 at step S103 is omitted. In other words, FIGS. 8 to 13 illustrate the example in which the single one-dimensional region of interest 44 has been set.

Figure 8:
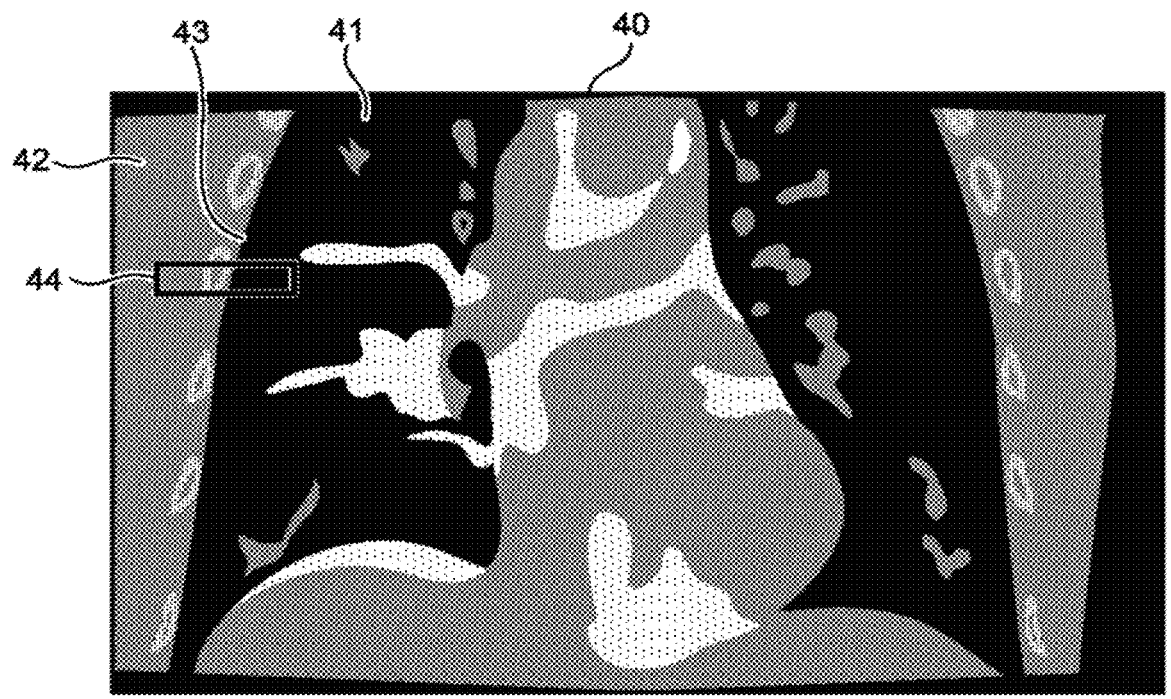
FIG. 8 is a drawing for explaining another example of the evaluating process according to the first embodiment.
Figure 9:
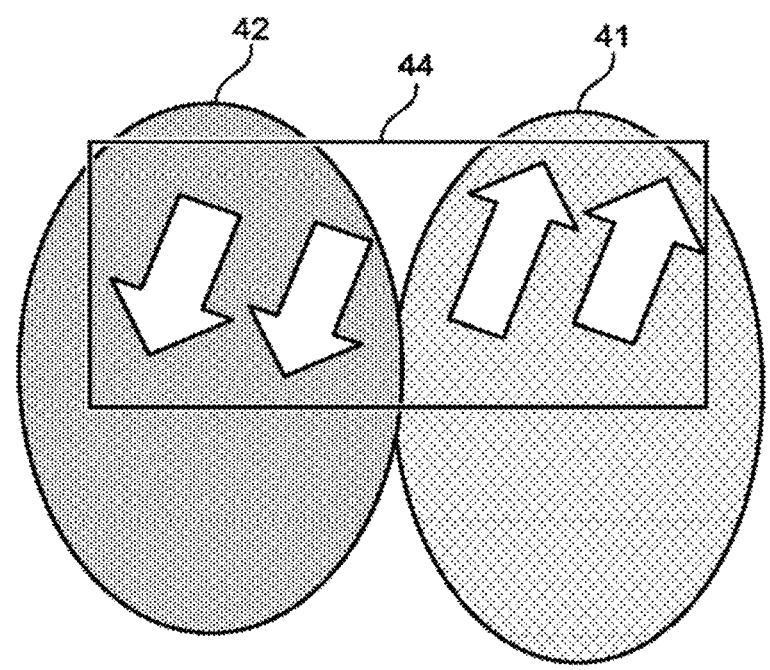
FIG. 9 is another drawing for explaining the example of the evaluating process according to the first embodiment.

A piece of three-dimensional image data 40 illustrated in FIG. 8 is a piece of data taken so as to include the lung field and the site outside the lung field of the subject P whose respiratory volume is relatively large. FIG. 9 illustrates a plurality of arrows indicating the orientations (the directions) and the magnitudes of the motion vectors of the plurality of pixels 45 in the region of interest 44 in FIG. 8. In FIG. 9, the orientations of the plurality of motion vectors are substantially summarized as two directions. Further, in FIG. 9, the magnitudes of the plurality of motion vectors are relatively large. The reason is that the respiratory volume of the subject P is relatively large.

Figure 10:
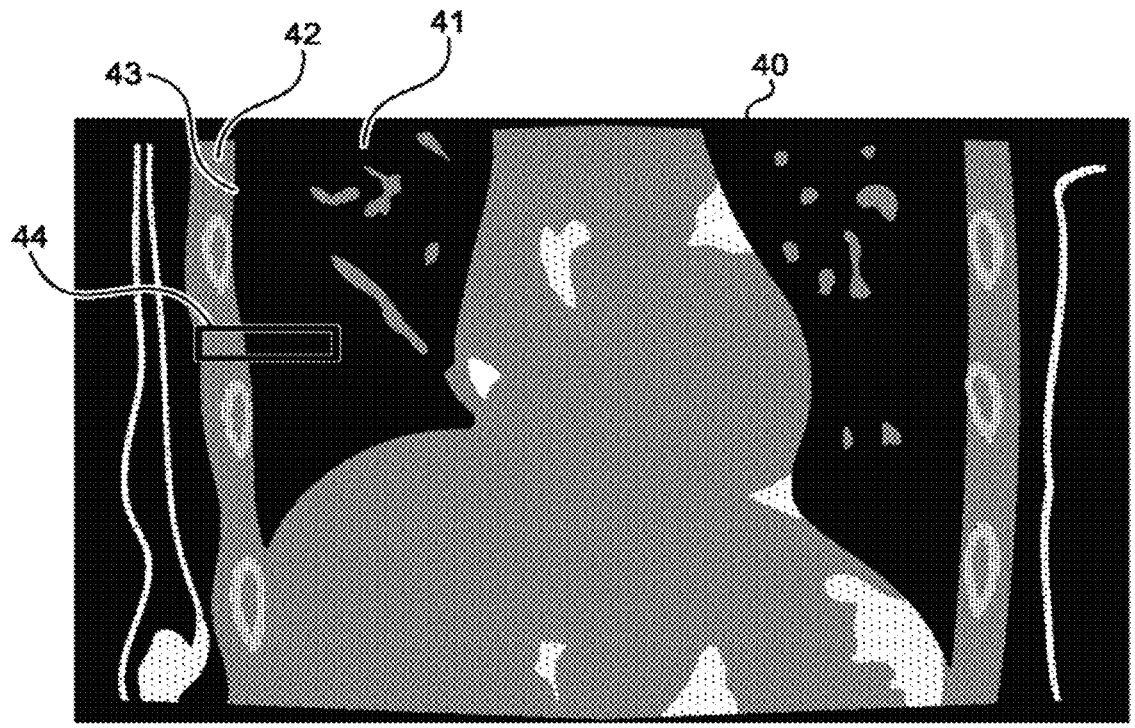
FIG. 10 is yet another drawing for explaining the example of the evaluating process according to the first embodiment.
Figure 11:
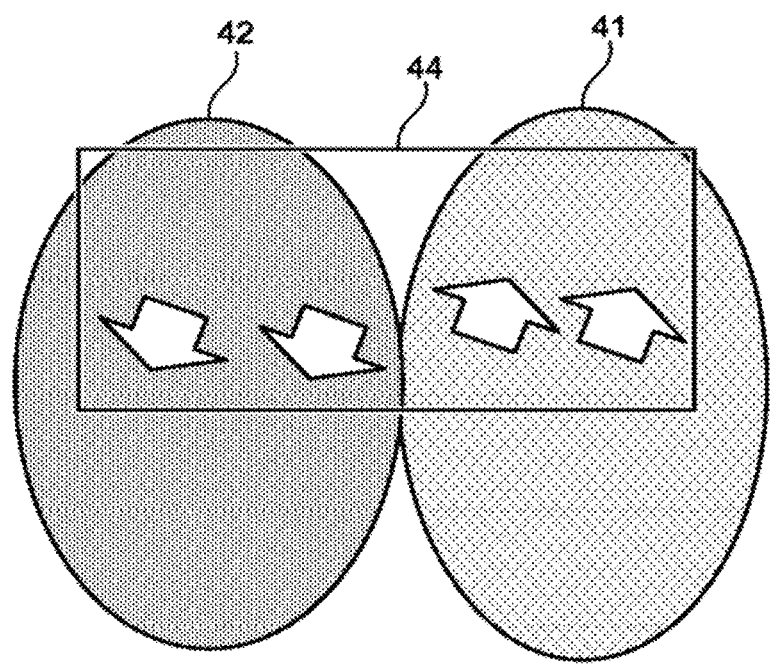
FIG. 11 is yet another drawing for explaining the example of the evaluating process according to the first embodiment.

In contrast, the piece of three-dimensional image data 40 illustrated in FIG. 10 is a piece of data taken so as to include the lung field and the site outside the lung field of the subject P whose respiratory volume is relatively small. FIG. 11 illustrates a plurality of arrows indicating the orientations and the magnitudes of the motion vectors of the plurality of pixels 45 in the region of interest 44 in FIG. 10. Similarly to FIG. 9, in FIG. 11, the orientations of the plurality of motion vectors are substantially summarized as two directions. It should be noted that, however, in FIG. 11 the magnitudes of the plurality of motion vectors are relatively small. The reason is that the respiratory volume of the subject P is relatively small.

Figure 12:
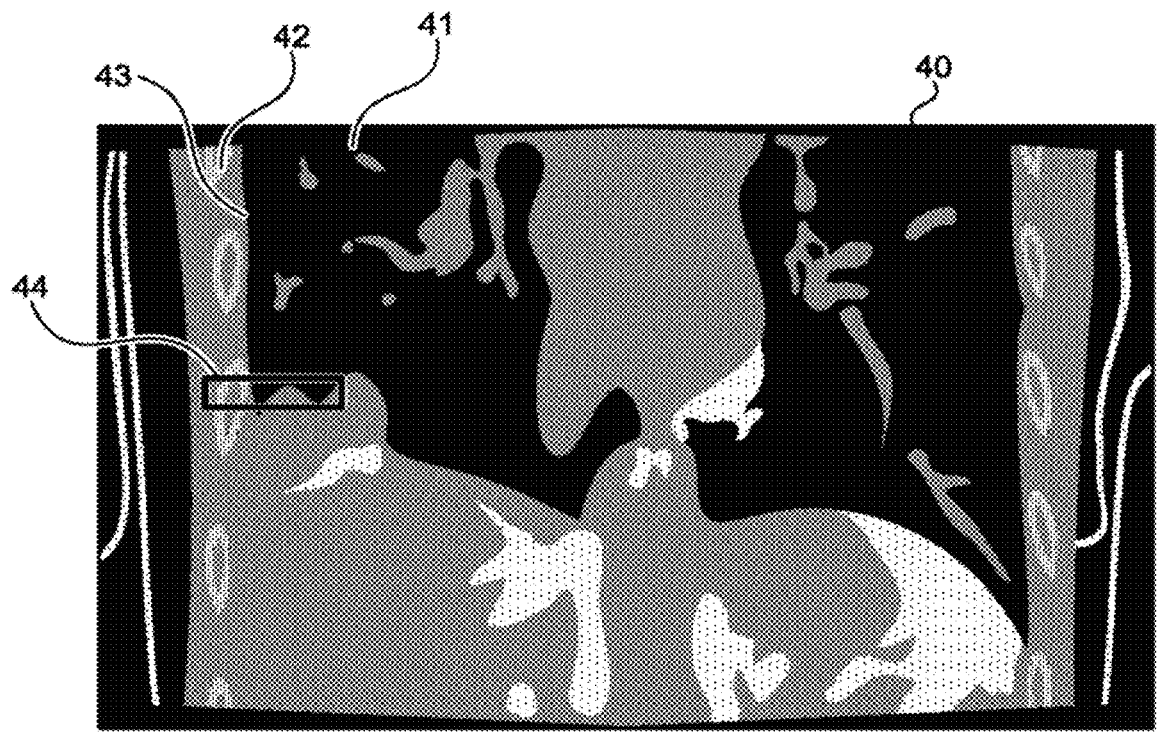
FIG. 12 is yet another drawing for explaining the example of the evaluating process according to the first embodiment.
Figure 13:
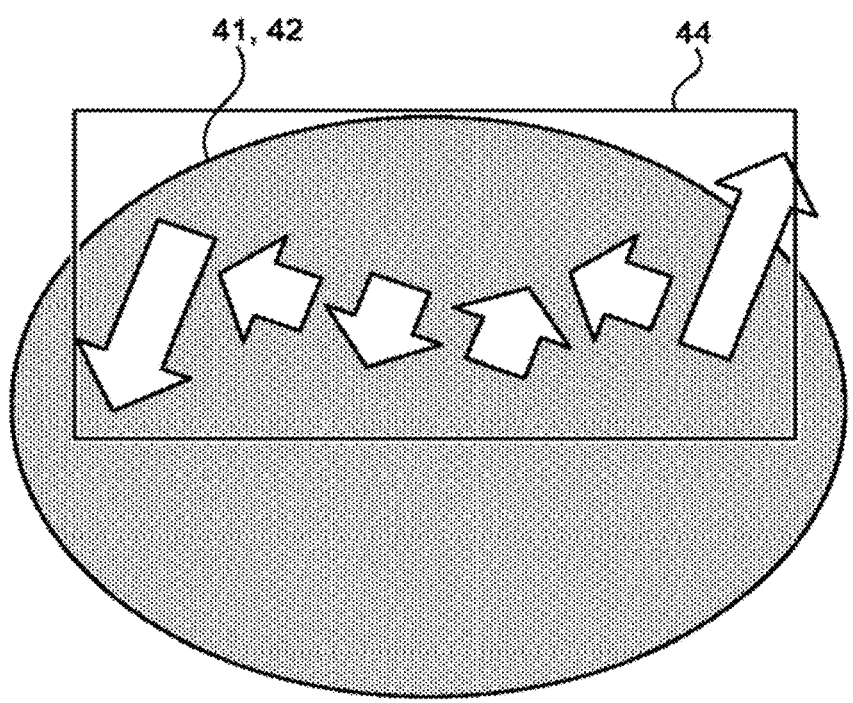
FIG. 13 is yet another drawing for explaining the example of the evaluating process according to the first embodiment.

Further, the piece of three-dimensional image data 40 illustrated in FIG. 12 is a piece of data taken so as to include the lung field and the site outside the lung field that are conglutinating with each other in one point. FIG. 13 illustrates a plurality of arrows indicating the orientations and the magnitudes of the motion vectors of the plurality of pixels 45 in the region of interest 44 in FIG. 12. In FIG. 13, the orientations and the magnitudes of the plurality of motion vectors are inhomogeneous. The reasons is that, because the lung field and the site outside the lung field of the subject P are conglutinating with each other in the one point, the site outside the lung field moves relative to the lung field in the manner of a pendulum, for example.

In the present embodiment, the evaluating function 347 is configured to calculate the probability p indicating the possibility of the occurrence of a conglutination, on the basis similarity among the motion vectors of the plurality of pix 45. For example, when the orientations and the magnitudes of the plurality of motion vectors are homogeneous, the evaluating function 347 calculates a value closer to "1" as the probability p, because it is considered that the region 41 of the lung field and the region 42 of the site outside the lung field are moving while conglutinating with each other. For example, when the orientations of the plurality of motion vectors are substantially the same as one another (substantially in one direction) and the magnitudes thereof are substantially equal to one another, the evaluating function 347 calculates a value closer to "1" as the probability p.

In contrast, when it is possible to substantially summarize the orientations of the plurality of motion vectors having substantially the same magnitude with one another as two directions, the evaluating function 347 calculates a value closer to "0" as the probability p because it is considered that the region 41 of the lung field and the region 42 of the site outside the lung field are moving independently of each other. For example, the evaluating function 347 calculates a value closer to "0" as the probability p, both when the respiratory volume of the subject P is relatively large as illustrated in FIGS. 9 and 10 and when the respiratory volume of the subject P is relatively small as illustrated in FIGS. 11 and 12. Consequently, according to the first embodiment, it is possible to evaluate the state of the conglutination with an excellent level of precision, not only when the respiratory volume is relatively large, but also when the respiratory volume is relatively small.

Further, when the orientations and the magnitudes of the plurality of motion vectors are inhomogeneous, the evaluating function 347 calculates a value closer to "1" as the probability p. For example, when the lung field and the site outside the lung field of the subject P are conglutinating with each other in one point as illustrated in FIGS. 12 and 13, the evaluating function 347 calculates a value closer to "1" as the probability p, because the orientations and the magnitudes of the plurality of motion vectors are inhomogeneous, and it is considered appropriate to have the plurality of pixels 45 belong to a single cluster. Consequently, according to the first embodiment, it is possible to evaluate the state of the conglutination with an excellent level of precision, even when the lung field and the site outside the lung field of the subject P are conglutinating with each other in one point.

As explained above, at step S106, the evaluating function 347 evaluates the state of the conglutination of the target site within the region of interest 44, on the basis of the result of the process performed as one part of the clustering process. Further, the evaluating function 347 calculates, as the index indicating the state of the conglutination, the probability p of the plurality of pixels 45 belonging to a single cluster when the clustering process is performed on the plurality of pixels 45, on the basis of the result of the process performed as the one part of the clustering process. Alternatively, the evaluating function 347 may calculate, as an index indicating the state of the conglutination, a probability (1–p) indicating a probability of the plurality of pixels 45 belonging to a plurality of (e.g., two) clusters when the clustering process is performed on the plurality of pixels 45, on the basis of the result of the process performed as the one part of the clustering process. In other words, the evaluating function 347 may calculate the index and evaluate the state of the conglutination, on the basis of the probability p of the plurality of pixels 45 belonging to mutually the same cluster, when the plurality of pixels 45 are classified into the two clusters (the first cluster and the second cluster mentioned above).

Further, at step S106, the evaluating function 347 calculates the probability p by using the weight $P(l_{j\_0})$, the weight $P(l_{j\_1})$, and the energy levels $E(L_1, L_2, \ldots, L_N, w)$ based on the motion vector $X_{n\_i}$ and the motion vector $X_{(n+1)\_i}$, and to further calculate the index on the basis of the probability p.

Further, at step S106, the evaluating function 347 calculates the index by using the energy levels $E(L_1, L_2, \ldots, L_N, w)$ based on the magnitudes of the difference vectors between the motion vectors $X_{n\_i}$ and the motion vectors $X_{(n+1)\_i}$ calculated at step S104.

After that, the evaluating function 347 brings values of the probability p into correspondence with the fourteen pixels 45 in the region of interest 44. For example, the evaluating function 347 generates correspondence information in which pieces of identification information identifying the pixels 45 are kept in correspondence with the values of the probability p and further stores the generated correspondence information into the memory 31.

Subsequently, the executing function 346 judges whether or not the region of interest 44 has been set over the entirety of the boundary 43 (step S107). When it is determined that the region of interest 44 has not been set over the entirety of the boundary 43 (step S107: No), the executing function 346 returns to step S102 where the executing function 346 sets a region of interest 44 in such a part of the entire boundary 43 where no region of interest 44 has yet been set. Further, the processes at steps S103 to S106 are repeatedly performed until the executing function 346 determines that the region of interest 44 has been set over the entirety of the boundary 43.

In contrast, when the executing function 346 determines that the region of interest 44 has been set over the entirety of the boundary 43 (step S107: Yes), the color assigning function 346 assigns a color corresponding to the probability p to each of the plurality of pixels structuring the three-dimensional image data (step S108).

For example, the color assigning function 348 obtains the correspondence information stored in the memory 31. After that, the color assigning function 346 assigns a color to each of the pixels according to correspondence relationships between the pieces of identification information and the values of the probability p indicated in the correspondence information. More specifically, to each of the pixels identified by the pieces of identification information, the color assigning function 348 assigns a color that corresponds to the probability p corresponding to the pixel. For example, the color assigning function 348 may assign the colors in such a manner that the closer the value of the probability p is to "1", the closer to red the color assigned to the pixel is and that the closer the value of the probability p is to "0", the closer to blue the color assigned to the pixel is. Further, to one or more pixels with which no value of the probability p is kept in correspondence, the color assigning function 348 may assign a predetermined color. In this situation, for example, the predetermined color may be a color other than the colors assigned to the pixels in accordance with the values of the probability p.

Further, the image processing function 344 generates display-purpose two-dimensional image data on the basis of the three-dimensional image data to which the colors have been assigned (step S109). For example, by performing a surface rendering process on the three-dimensional image data, the image processing function 344 generates surface rendering image data as the display-purpose two-dimensional image data.

Figure 14:
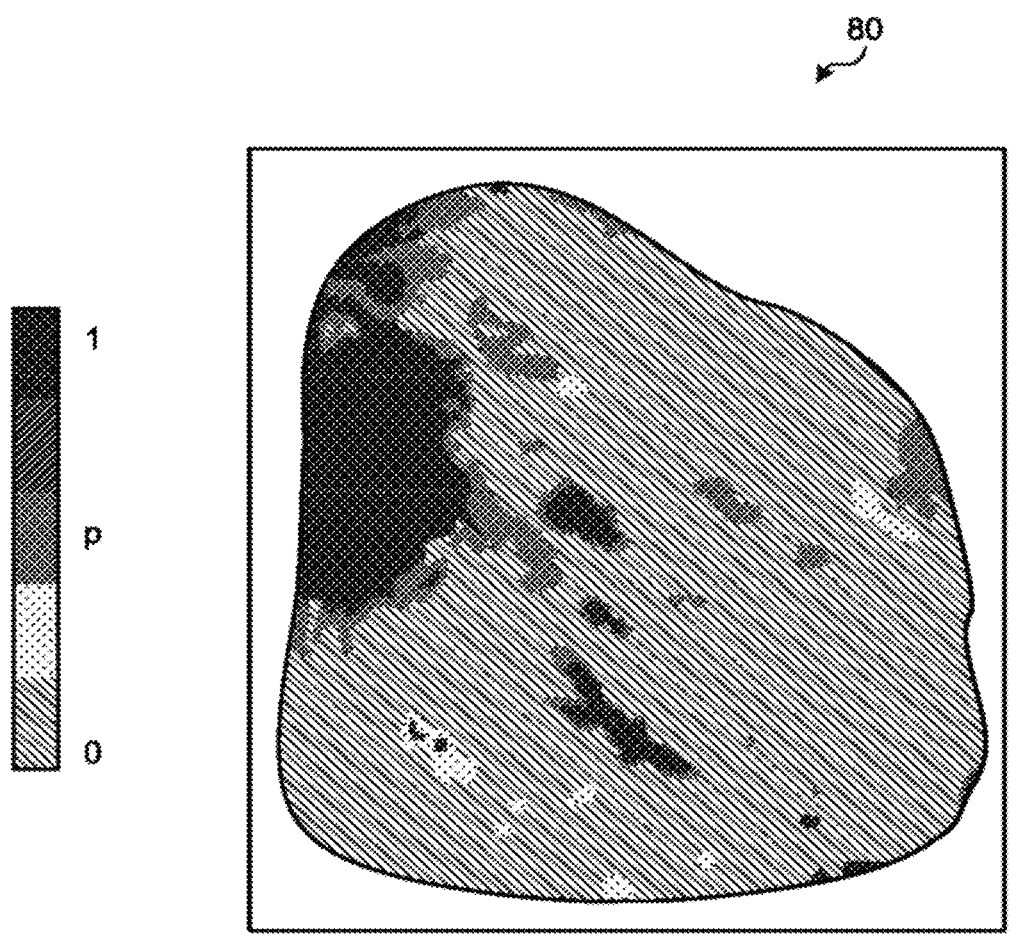
FIG. 14 is a drawing illustrating an example of an image represented by display-purpose two-dimensional image data according to the first embodiment.

After that, the system controlling function 341 causes the display device 32 to display an image represented by the display-purpose two-dimensional image data (step S110) and ends the evaluating process. FIG. 14 is a drawing illustrating an example of the image represented by the display-purpose two-dimensional image data according to the first embodiment. For example, as illustrated in FIG. 14, the system controlling function 341 causes the display device 32 to display a surface rendering image 80 represented by the surface rendering image data. In this manner, the system controlling function 341 causes the display device 32 to display a result of the evaluation made by the evaluating function 347. As a result, by referring to the surface rendering image 80, the operator is able to easily understand which part of the target site has a high possibility of having a conglutination.

The X-ray CT apparatus 1 according to the first embodiment has thus been explained. As explained above, by using the X-ray CT apparatus 1, it is possible to evaluate the state of the adhesion with an excellent level of precision.

First Modification Example of First Embodiment

In the first embodiment above, the example is explained in which the one-dimensional region of interest 44 is set; however, the region of interest 44 does not necessarily have to be one-dimensional and may be two-dimensional or three-dimensional, for example. Thus, an example with such a modification will be explained as a first modification example of the first embodiment. In the first modification example, the X-ray CT apparatus 1 is configured to perform the same processes as those in the first embodiment by using the pixels in the region of interest 44 that is two- or three-dimensional.

For example, in the first modification example, in the two-dimensional region of interest 44, a plurality of pixel rows are arranged in the direction orthogonal to the direction of the line normal to the boundary 43, the pixel rows each being structured with a plurality of pixels that are linearly (one-dimensionally) arranged along the direction of the line normal to the boundary 43. Thus, in the first modification example, the X-ray CT apparatus 1 is configured to perform the same processes as those performed on the plurality of pixels 45 linearly (one-dimensionally) arranged in the first embodiment, on each of the plurality of pixel rows.

Further, also when a three-dimensional region of interest 44 is set, the executing function 346 is configured to perform the same processes as those performed when the two-dimensional region of interest 44 is set. Consequently, the first modification example is able to achieve the same advantageous effects as those achieved by the first embodiment.

Second Modification Example of First Embodiment

Further, in e first embodiment and the first modification example, the example was explained in which the executing function 346 performs the one part of the clustering process; however, the executing function 346 may perform the entirety of the clustering process. In that situation, the executing function 346 performs the clustering process of classifying each of the pixels 45 into a corresponding one of the clusters, by using the cut line corresponding to the smallest energy level $E(L_1, L_2, \ldots, L_N, w)$ among the energy levels $E(L_1, L_2, \ldots, L_N, w)$ calculated with respect to the fifteen cut lines. In other words, the executing function 346 performs the entirety of the clustering process.

In this manner, the executing function 346 performs the clustering process of classifying each of the plurality of pixels 45 into one selected from between the first cluster and the second cluster, on the basis of the energy levels $E(L_1, L_2, \ldots, L_N, w)$ based on the motion vector $X_{n\_i}$ and the motion vector $X_{(n+1)\_i}$. In other words, the executing function 346 performs the clustering process on the basis of the motion vector $X_{n\_i}$ and the motion vector $X_{(n+1)\_i}$.

Further, when performing the entirety of the clustering process, the X-ray CT apparatus 1 may calculate a degree of reliability indicating likelihood of the probability p, by using the result of the clustering process. Thus, an example with such a modification will be explained as a second modification example of the first embodiment.

Figure 15:
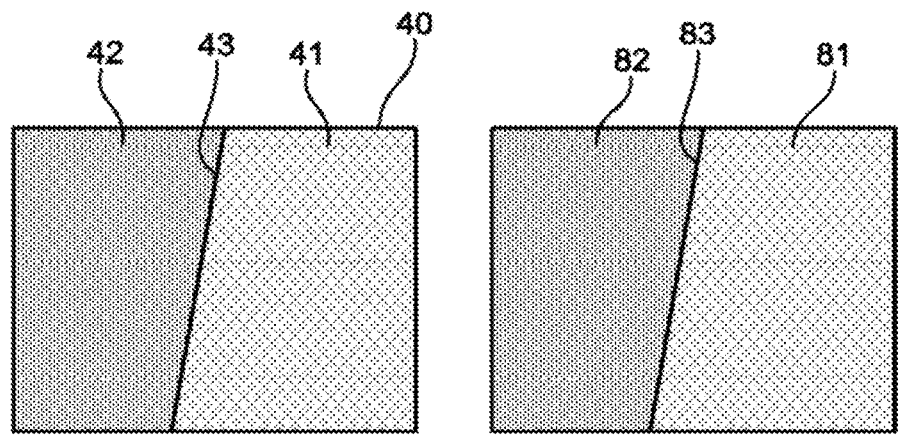
FIG. 15 is a drawing for explaining an example of a process performed by an X-ray CT apparatus according to a second modification example.
Figure 16:
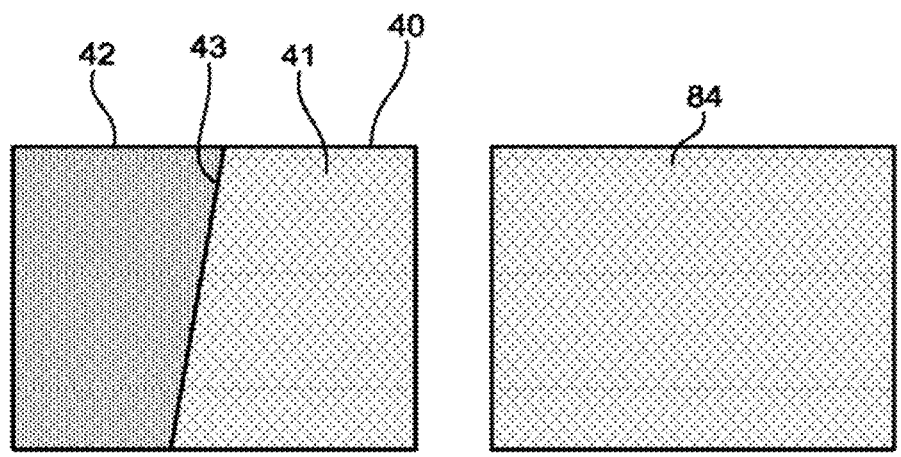
FIG. 16 is another drawing for explaining the example of the process performed by the X-ray CT apparatus according to the second modification example.

FIGS. 15 and 16 are drawings for explaining an example of a process performed by an X-ray CT apparatus according to the second modification example. FIG. 15 illustrates the region 41 of the lung field and the region 42 of the site outside the lung field extracted by the segmentation function 345 from the three-dimensional image data 40. Further, FIG. 15 illustrates a region 82 in which the pixels 45 classified into the first cluster by the executing function 346 are positioned and a region 81 in which the pixels 45 classified into the second cluster by the executing function 346 are positioned.

Further, in the second modification example, the evaluating function 347 calculates, as the degree of reliability indicating the likelihood of the probability p, a degree of coincidence between: the boundary 43 formed between the region 41 of the lung field and the region 42 of the site outside the lung field; and a boundary 83 formed between the region 81 and the region 82. In this situation, as a method for calculating the degree of coincidence, the evaluating function 347 uses a publicly-known method.

In this situation, when the degree of coincidence between the boundary 43 and the boundary 83 is high, it means that the degree of coincidence between the result of the clustering process and the result of the segmentation process is also high. The higher the degree of coincidence is between the result of the clustering process and the result of the segmentation process, the higher is the degree of reliability indicating the likelihood of the result of the clustering process. When the degree of reliability indicating the likelihood of the result of the clustering process is high, it means that the degree of reliability indicating the likelihood of the probability p is also high.

Accordingly, the evaluating function 347 according to the second modification example is configured to calculate the degree of coincidence between the boundary 43 and the boundary 83 as the degree of reliability indicating the likelihood of the probability p.

Further, an example will be explained in which the executing function 346 has classified the pixels 45 in such a manner that all the pixels 45 in the region of interest 44 belong to the second cluster. In that situation, as illustrated in FIG. 16, the region 81 is present in which the pixels 45 belonging to the second cluster are positioned, but there is no region in which pixels 45 belonging to the first cluster are positioned. For this reason, no boundary is present between the region 81 and a region in which pixels 45 belonging to the first cluster are positioned. When no boundary is present like in this situation, the evaluating function 347 is configured to calculate a predetermined value (e.g., "0") as the degree of reliability indicating the likelihood of the probability p. Similarly, when the executing function 346 has classified the pixels 45 in such a manner that all the pixels 45 in the region of interest 44 belong to the first cluster, the evaluating function 347 is configured to calculate the predetermined value (e.g., "0") as the degree of reliability.

In this manner, the evaluating function 347 calculates the degree of reliability of the evaluation result for the state of conglutination, on the basis of the result of the segmentation process and the result of the clustering process.

After that, the system controlling function 341 according to the second modification example causes the display device 32 to display the calculated degree of reliability.

The X-ray CT apparatus 1 according to the second modification example has thus been explained. According to the second modification example, it is possible to quantitatively display the degree of reliability indicating the likelihood of the probability p. Consequently, according to the second modification example, it is possible to enable the operator to understand the likelihood of the probability p with a higher level of certainty.

Second Embodiment

It is possible to arrange an image processing apparatus connected to the X-ray CT apparatus 1 via a network so as to have the functions of the X-ray CT apparatus 1 according to the first embodiment, the first modification example, or the second embodiment. Such an embodiment will be explained as a second embodiment, with reference to FIG. 17.

Figure 17:
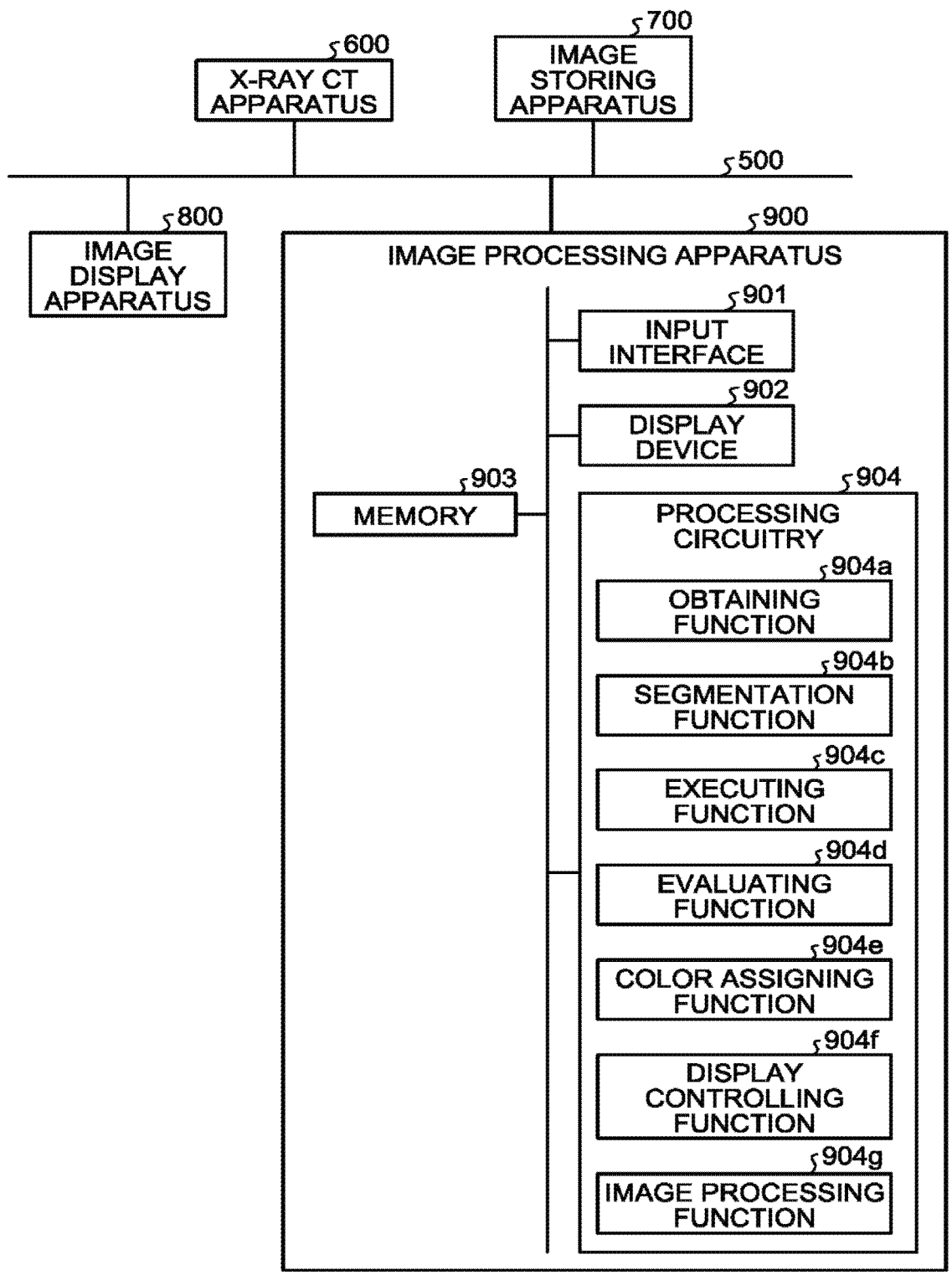
FIG. 17 is a drawing illustrating an exemplary configuration of a system including an image processing apparatus according to a second embodiment.

FIG. 17 is a drawing illustrating an exemplary configuration of a system including the image processing apparatus according to the second embodiment. The system illustrated in the example in FIG. 17 includes an X-ray CT apparatus 600, an image storing apparatus 700, an image display apparatus 800, and an image processing apparatus 900. The X-ray CT apparatus 600, the image storing apparatus 700, the image display apparatus 800, and the image processing apparatus 900 are able to communicate with one another either directly or indirectly via an intra-hospital Local Area Network (LAN) 500 installed in a hospital, for example. For example, when a Picture Archiving and Communication System (PACS) has been introduced, the apparatuses 600, 700, 800, and 900 transmit and receive images and the like to and from one another according to a Digital Imaging and Communications in Medicine (DICOM) standard.

The X-ray CT apparatus 600 is the X-ray CT apparatus 1 according to the first embodiment, the first modification example, or the second modification example. The X-ray CT apparatus 600 is configured to transmit four-dimensional image data (pieces of three-dimensional image data corresponding to T frames) image processing apparatus 900.

The image storing apparatus 700 is a database configured to store therein display-purpose two-dimensional image data generated by the X-ray CT apparatus 600 and the image processing apparatus 900.

The image processing apparatus 900 is a workstation having the functions of the X-ray CT apparatus 1 according to the first embodiment, the first modification example, or the second modification example. The image processing apparatus 900 is configured to perform the same processes as those performed by the X-ray CT apparatus 1 according to the first embodiment, the first modification example, or the second modification example, by using the pieces of three-dimensional image data corresponding to the T frames and having been transmitted thereto from the X-ray CT apparatus 600.

The image processing apparatus 900 includes an input interface 901, a display device 902, a memory 903, and processing circuitry 904.

The input interface 901 is configured to receive input operations of various types of instructions and various types of information from the operator. More specifically, the input interface 901 is connected to the processing circuitry 904 and is configured to convert the input operations received from the operator into electrical signals and to output the electrical signals to the processing circuitry 904. For example, the input interface 901 is realized by using a trackball, a switch button, a mouse, a keyboard, a touch pad on which input operations are performed by touching the operation surface thereof, a touch screen in which a display screen and a touch pad are integrally formed, a contactless input interface using an optical sensor, an audio input interface, and/or the like. In the present disclosure, the input interface 901 does not necessarily have to include one or more physical operational component parts such as a mouse, a keyboard, and/or the like. Examples of the input interface 901 include, for instance, electrical signal processing circuitry configured to receive an electrical signal corresponding to an input operation from an external input device provided separately from the apparatus and to output the electrical signal to the processing circuitry 904.

The display device 902 is configured to display various types of information and various types of images. More specifically, the display device 902 is connected to the processing circuitry 904 and is configured to convert data of the various types of information and the various types of images sent thereto from the processing circuitry 904 into display-purpose electrical signals and to output the display-purpose electrical signals. For example, the display device 902 may be realized by using a liquid crystal monitor, a Cathode Ray Tube (CRT) monitor, a touch panel, or the like.

The memory 903 is configured to store therein various types of data. More specifically, the memory 903 is configured to store therein various types of images. For example, the memory 903 is realized by using a semiconductor memory element such as a Random Access Memory (RAM), a flash memory, or the like, or a hard disk, an optical disk, or the like.

The processing circuitry 904 is configured to exercise overall control of the image processing apparatus 900. For example, when having received the pieces of three-dimensional image data corresponding to the T frames and having transmitted thereto from the X-ray CT apparatus 600, the processing circuitry 904 stores the received pieces of three-dimensional image data into the memory 903. The processing circuitry 904 is realized by using a processor. The processing circuitry 904 includes an obtaining function 904a, a segmentation function 904b, an executing function 904c, an evaluating function 904d, a color assigning function 904e, a display controlling function 904f, and an image processing function 904g. The obtaining function 904a is an example of an obtaining unit. The segmentation function 904b is an example of a segmentation processing unit. The executing function 904c is an example of an executing unit. The evaluating function 904d is an example of an evaluating unit. The display controlling function 904f is an example of a display controlling unit. The image processing function 904g is an example of a generating unit.

In this situation, for example, the functions of the constituent elements of the processing circuitry 904, namely, the obtaining function 904a, the segmentation function 904b, the executing function 904c, the evaluating function 904d, the color assigning function 904e, the display controlling function 904f, and the image processing function 904g are stored in the memory 903 in the form of computer-executable programs. The processing circuitry 904 is configured to realize the functions by reading the programs from the memory 903 and executing the read programs. In other words, the processing circuitry 904 that has read the programs has the functions illustrated within the processing circuitry 904 in FIG. 17.

The obtaining function 904a is configured to obtain the pieces of three-dimensional image data corresponding to the T frames and being stored in the memory 903. In other words, the obtaining function 904a is configured to obtain the plurality of pieces of three-dimensional image data taken so as to include a target site of the subject P in a plurality of temporal phases.

The segmentation function 904b is configured to perform the same process as the process at step S101 explained above. The executing function 904c is configured to perform the same processes as the processes at steps S102 to S103 and S107 explained above. The evaluating function 904d is configured to perform the same process as the process at step S106 explained above.

The color assigning function 904e is configured to perform the same process as the process at step S108 explained above. The image processing function 904g is configured to perform the same process as the process at step S109 explained above. The display controlling function 904f is configured to perform tree same process as the process at step S110 explained above.

The image processing apparatus 900 according to the second embodiment has thus been explained. By using the image processing apparatus 900, it is possible to evaluate the state of the adhesion with an excellent level of precision, in the same manner as in the first embodiment, the first modification example, and the second modification example.

According to at least one aspect of the embodiments and the modification examples described above, it is possible to evaluate the state of the adhesion with an excellent level of precision.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising processing circuitry configured:
    to obtain a plurality of images taken so as to include a target site of a subject in a plurality of temporal phases; and
    to calculate an index indicating a state of an adhesion at a boundary between a first site of the subject corresponding to a first region and a second site of the subject corresponding to a second region, by using classification information used for classifying each of a plurality of pixels into one selected from between a first class related to the first region and a second class related to a second region positioned adjacent to the first region in a predetermined direction, on a basis of mobility information among the images in the plurality of temporal phases with respect to the plurality of pixels in the images that are arranged in the predetermined direction across the boundary between the first region and the second region of the images, wherein, when classifying the pixels into the first and the second classes, the processing circuitry evaluates the state of the adhesion by calculating the index on a basis of a probability of the plurality of pixels belonging to a mutually same class.

2. The image processing apparatus according to claim 1, wherein the processing circuitry is configured to: calculate the probability by using a value related to a cost that is based on the mobility information and is used for classifying each of the pixels into one selected from between the first class and the second class, and calculate the index on the basis of the calculated probability.

3. The image processing apparatus according to claim 1, wherein
    as the mobility information, the processing circuitry calculates a motion vector of each of the plurality of pixels,
    with respect to each pair of two pixels that are positioned adjacent to each other in the predetermined direction among the plurality of pixels, the processing circuitry calculates a magnitude of a difference vector of two motion vectors of the two pixels, on a basis of the calculated plurality of motion vectors, and
    the processing circuitry calculates the index on a basis of the calculated magnitudes of the difference vectors.

4. The image processing apparatus according to claim 1, wherein
    the processing circuitry performs a segmentation process to extract the first region and the second region from each of the images,
    the processing circuitry performs a clustering process to classify each of the plurality of pixels into one selected from between the first class and the second class on the basis of the mobility information, and
    the processing circuitry calculates a degree of reliability of the index, on a basis of a result of the segmentation process and a result of the clustering process.

5. The image processing apparatus according to claim 4, wherein the processing circuitry causes a display to display the degree of reliability.

6. The image processing apparatus according to claim 1, wherein the processing circuitry causes a display to display the index.

7. The image processing apparatus as claimed in claim 1, wherein the classification information comprises energy levels.

8. The image processing apparatus as claimed in claim 1, wherein the classification information is acquired by performing a part of a graph cut process.

9. A medical image taking apparatus comprising processing circuitry configured:
to generate a plurality of images taken so as to include a target site of a subject in a plurality of temporal phases; and
to calculate an index indicating a state of an adhesion at a boundary between a first site of the subject corresponding to a first region and a second site of the subject corresponding to a second region, by using classification information used for classifying each of a plurality of pixels into one selected from between a first class related to the first region and a second class related to a second region positioned adjacent to the first region in a predetermined direction, on a basis of mobility information among the images in the plurality of temporal phases with respect to the plurality of pixels in the images that are arranged in the predetermined direction across the boundary between the first region and the second region of the images, wherein, when classifying the pixels into the first and the second classes, the processing circuitry evaluates the state of the adhesion by calculating the index on a basis of a probability of the plurality of pixels belonging to a mutually same class.

10. The medical image taking apparatus as claimed in claim 9, wherein the classification information comprises energy levels.

11. The medical image taking apparatus as claimed in claim 9, wherein the classification information is acquired by performing a part of a graph cut process.

12. An image processing apparatus comprising processing circuitry configured:
to obtain a plurality of images taken so as to include a target site of a subject in a plurality of temporal phases;
to perform a segmentation process to extract a first region and a second region from each of the images;
to calculate an index indicating a state of an adhesion at a boundary between a first site of the subject corresponding to the first region and a second site of the subject corresponding to the second region, by performing a clustering process using classification information used for classifying each of a plurality of pixels into one selected from between a first class related to the first region and a second class related to a second region positioned adjacent to the first region in a predetermined direction, on a basis of mobility information among the images in the plurality of temporal phases with respect to the plurality of pixels in the images that are arranged in the predetermined direction across the boundary between the first region and the second region of the images; and
to calculate a degree of reliability of the index, on a basis of a result of the segmentation process and a result of the clustering process.

13. The image processing apparatus according to claim 12, wherein the processing circuitry is configured to cause a display to display the degree of reliability.

* * * * *